United States Patent [19]

Nakanishi et al.

[11] Patent Number: 5,158,963
[45] Date of Patent: Oct. 27, 1992

[54] 1-4-DIHYDROPYRIDINE DERIVATIVE, PROCESS FOR PREPARING THE SAME AND PHARMACEUTICAL COMPOSITION CONTAINING THE SAME

[75] Inventors: Michio Nakanishi, Toyonaka; Katsuhiro Uchida, Kyoto; Terutake Nakagawa, Otsu; Kiyoharu Ukai; Michiko Nagahara, both of Shiga; Jun Nakano, Moriyama; Kazuhiko Kimura, Otsu, all of Japan

[73] Assignee: Kaken Pharmaceutical Co., Ltd., Tokyo, Japan

[21] Appl. No.: 557,816

[22] Filed: Jul. 26, 1990

[30] Foreign Application Priority Data

Aug. 2, 1989 [JP] Japan .................. 1-200470

[51] Int. Cl.⁵ .............. A61K 31/455; C07D 211/86
[52] U.S. Cl. ................... 514/356; 514/318; 514/212; 514/210; 514/343; 546/321; 546/194; 546/283; 540/597
[58] Field of Search .......... 546/321, 194, 283; 540/597; 514/356, 318, 212, 210, 343

[56] References Cited

U.S. PATENT DOCUMENTS

| | | | |
|---|---|---|---|
| 4,492,703 | 1/1985 | Goldmann et al. | 546/321 |
| 4,497,808 | 2/1985 | Zimmermann et al. | 546/321 |
| 4,510,310 | 4/1985 | Wehinger et al. | 546/321 |
| 4,849,433 | 7/1989 | Wehinger et al. | 514/356 |
| 4,874,773 | 10/1989 | Hisaki et al. | 514/355 |

FOREIGN PATENT DOCUMENTS

| | | |
|---|---|---|
| 70473/81 | 11/1981 | Australia. |
| 0026317 | 4/1981 | European Pat. Off.. |
| 0039863 | 11/1981 | European Pat. Off.. |
| 245918 | 11/1987 | European Pat. Off.. |
| 2405658 | 8/1974 | Fed. Rep. of Germany. |
| 1409865 | 10/1975 | United Kingdom. |

*Primary Examiner*—Jane T. Fan
*Attorney, Agent, or Firm*—Armstrong & Kubovcik

[57] ABSTRACT

A 1,4-dihydropyridine derivative having the formula (I):

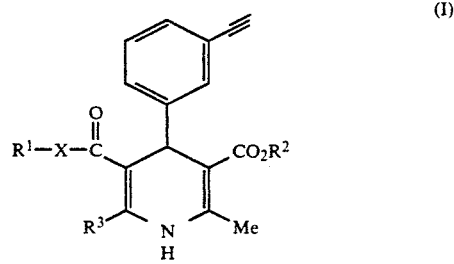

wherein X is oxygen atom or nitrogen atom; when X is oxygen atom, $R^1$ is hydrogen atom, a lower alkyl group, a lower cycloalkyl group, a lower alkenyl group or magnesium atom, when X is nitrogen atom, $X\text{-}R^1$ group is $NH_2$, $NHR^{1'}$, $NR^{1'}R^{1''}$ or

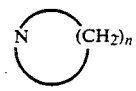

in which $R^{1'}$ is a lower alkyl group or a lower alkoxyalkyl group, $R^{1''}$ is a lower alkyl group and n is an integer of 2 to 6; $R^2$ is a lower alkyl group, a lower cycloalkyl group or a lower alkoxyalkyl group and $R^3$ is a lower alkyl group, formyl group, dimethoxymethyl group, cyano group or amino group, when X is oxygen atom and $R^1$ is hydrogen atom or magnesium atom, $R^3$ is methyl group, when X is nitrogen atom, $R^3$ is methyl group, or a pharmaceutically acceptable salt thereof, some processes for preparing the same and a pharmaceutical composition containing the same. According to the present invention, a superior cerebral function improver can be provided.

16 Claims, 1 Drawing Sheet

1-4-DIHYDROPYRIDINE DERIVATIVE, PROCESS FOR PREPARING THE SAME AND PHARMACEUTICAL COMPOSITION CONTAINING THE SAME

BACKGROUND OF THE INVENTION

The present invention relates to a 1,4-dihydropyridine derivative, more particularly to a 4-(3-ethynyl)phenyl-1,4-dihydropyridine, a process for preparing the same and a pharmaceutical composition containing the same. The present invention is a useful invention in medical field.

Hitherto, many 1,4-dihydropyridine derivatives have been known as compounds having pharmacological activities such as vasodepressor activity and vasodilator activity. For example, it is known that dimethyl 2,6-dimethyl-4-(2-nitrophenyl)-1,4-dihydropyridine-3,5-dicarboxylate (hereinafter referred to as "nifedipine") has strong pharmacological activities such as vasodepressor activity and coronary vasodilator activity (U.S. Pat. No. 3,644,627). Also, 2-(N-benzyl-N-methylamino)ethyl, methyl 2,6-dimethyl-4-(3-nitrophenyl)-1,4-dihydropyridine-3,5-dicarboxylate hydrochloride (hereinafter referred to as "nicardipine") (U.S. Pat. No. 3,985,758) and isopropyl, 2-methoxyethyl 2,6-dimethyl-4-(3-nitrophenyl)-1,4-dihydropyridine-3,5-dicarboxylate (hereinafter referred to as "nimodipine") are extensively known.

Most of well-known 1,4-dihydropyridine derivatives are compounds in which phenyl group at the 4-position of pyridine ring is substituted by nitro group, a halogen and the like. Examples of the compounds in which the phenyl group at the 4-position is substituted by acetylene are few. For example, with respect to the process for preparing 4-(2-ethynylphenyl)-2,6-dialkyl-1,4-dihydropyridine-3,5-dicarboxylic acid ester which has been patented as a process, an alkyne group is exemplified as the substituent in a part of the process (Japanese Examined Patent Publication No. 12632/1976). However, the compound is not concretely described in which the phenyl group at the 4-position of pyridine ring is substituted by an alkyne group since no Example as to such compound is shown. Namely, physical property and pharmacological activity of such compound are unknown. Also, 4-[2-(2-aryl)ethynyl]phenyl-2,6-dimethyl-1,4-dihydropyridine-3,5-dicarboxylic acid dialkyl ester is disclosed in Japanese Unexamined Patent Publication No. 252768/1987. However, detailed pharmacological activity is not described. It is surmised that the use thereof as a medicament is an antihypertensive agent.

On the other hand, tissue selectivity and strength of activity of well-known cerebral function improvers are not sufficient. Therefore, because antihypertensive activity is a side effect for cerebral function improvers, a cerebral function improver had been desired which has weak antihypertensive activity and more superior tissue selectivity for cerebrum.

Calcium antagonists such as well-known 1,4-dihydropyridine derivatives as typical examples were drugs which have antihypertensive activity as main drug efficacy and cerebrocirculation improvement activity as secondary drug efficacy. In the treatment of a series of diseases which are generically named as cerebral failure and cerebral circulatory disturbance, antihypertensive activity is side effect rather than drug efficacy. The present invention provides a cerebral function improver which has superior tissue selectivity for cerebrum, weak antihypertensive activity and moreover has cerebroprotective activity, cerebroactivating activity and cerebrocirculation improvement activity.

As the result of the continuous effort and detailed investigation of pharmacological activity with respect to 1,4-dihydropyridine derivatives having phenyl group at the 4-position of pyridine ring substituted by acetylene group of the present inventors, now it has been found that compounds having superior tissue selectivity for cerebrum, weak antihypertensive activity, and moreover having cerebroprotective activity, cerebroactivating activity and cerebrocirculation improvement activity. Consequently, the present invention has been accomplished.

That is, in a series of diseases such as cerebral arterial sclerosis, cerebral hemorrhage, cerebral infarction and traumatic cerebral lesion, cerebrum becomes ischemic and cerebral nerve cells are excessively excited. The function of cerebral nerve cells is disturbed. Eventually it is considered that patients with the series of diseases fall into cerebral hypofunction, dysmnesia and dementia (See D. M. Woodbury, Psychiat. Neurol. Neurochir., 74, page 91, 1971). Also, it is considered that excessive excitation of cerebral nerve cells in case of ischemia is similar to excitation in case of ictus epilepticus. Therefore, a compound capable of inhibiting excessive excitation of cerebral nerve cells can be a preventive and therapeutic agent of the above-mentioned diseases as a cerebroprotective drug.

Flunarizine being a calcium antagonist which is regarded as highly specific for cerebrum is used as a cerebral circulation improver. However, it is reported that flunarizine induces side effects such as Parkinson symptom and depression symptom caused by central nervous system inhibitory activity when flunarizine is administered over an extended period of time (See Lugaresi A., Eur. Neurol., 28, pages 208-211, 1988). Accordingly, a cerebral function improver is desired which has accelative activity (cerebroactivating activity) rather than inhibitory activity for central nervous system without such side effects.

Cerebrocirculation improvement activity in case of ischemia is effective as a prevention and therapy of a series of diseases such as cerebral arterial selerosis, cerebral hemorrhage, cerebral infarction and traumatic cerebral lesion.

Thus it is possible that a compound having all of cerebroprotective activity, cerebroactivating activity and cerebrocirculation improvement activity becomes a superior cerebral function improver.

Concretely, as evaluation of cerebroprotective activity the compound of the present invention showed an effect equal to that of the antiepileptic agent diphenylhydantoin as a positive control in a test of convulsion induced by pentylenetetrazole in mice. The effect of the compound according to the present invention was stronger than those of nicardipine and nimodipine which are recognized as calcium antagonists having high selectivity for cerebrum. Also, in a test of maximal electroshock-induced seizures in mice it was recognized that the compound of the present invention was effective, and the compound of the present invention was stronger than flunarizine which is recognized as the well-known calcium antagonist having high selectivity for cerebrum. In the above test nimodipine was ineffective. As evaluation of cerebroactivating activity, in a forced swimming test in mice, although the compound of the present invention was effective, nimodipine and flunarizine were ineffective. Cerebrocirculation improvement activity was evaluated by decapitation induced hypoxia test in mice and a test of cerebrocortical blood flow increasing in rabbits. In the decapitation induced hypoxia test in mice, the compound of the present invention showed an effect equal to that of flunarizine and stronger effect than those of nimodipine and nicardipine. In the test of cerebrocortical blood flow increasing in rabbits, it was observed that the compound of the present invention showed stronger effect than that of flunarizine. Vasodepressor activity was evaluated in normal rats. Although nicardipine showed strong antihypertensive activity, on the contrary, in the compound of the present invention significant antihypertensive activity was not observed in a dose which shows the above-mentioned drug efficacy.

It is an object of the invention to provide a 1,4-dihydropyridine derivative having the formula (I) having all of cerebroprotective activity, cerebroactivating activity and cerebrocirculation improvement activity.

A further object of the invention is to provide processes for preparing the same.

It is a still further object of the invention to provide a composition containing the same useful for a superior cerebral function improver.

These and the other objects of the present invention will become apparent from the description hereinafter.

SUMMARY OF THE INVENTION

In accordance with the present invention, there are provided a 1,4-dihydropyridine derivative having the formula (I):

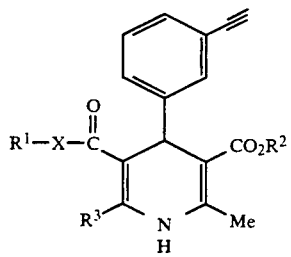

(I)

wherein X is oxygen atom or nitrogen atom; when X is oxygen atom, $R^1$ is hydrogen atom, a lower alkyl group, a lower cycloalkyl group, a lower alkenyl group or magnesium atom, when X is nitrogen atom, X—$R^1$ group is $NH_2$, $NHR^{1'}$, $NR^{1'}R^{1''}$ or

in which $R^{1'}$ is a lower alkyl group or a lower alkoxyalkyl group, $R^{1''}$ is a lower alkyl group and n is an integer of 2 to 6; $R^2$ is a lower alkyl group, a lower cycloalkyl group or a lower alkoxyalkyl group and $R^3$ is a lower alkyl group, formyl group, dimethoxymethyl group, cyano group or amino group, when X is oxygen atom and $R^1$ is hydrogen atom or magnesium atom, $R^3$ is methyl group, when X is nitrogen atom, $R^3$ is methyl group, or a pharmaceutically acceptable salt thereof, a process for preparing a 1,4-dihydropyridine derivative having the formula (I):

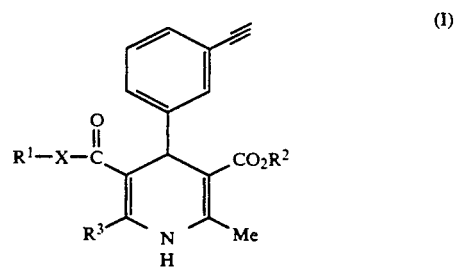

(I)

wherein X is oxygen atom or nitrogen atom; when X is oxygen atom, $R^1$ is a lower alkyl group, a lower cycloalkyl group or a lower alkenyl group, when X is nitrogen atom, X—$R^1$ group is $NH_2$, $NHR^{1'}$, $NR^{1'}R^{1''}$ or

in which $R^{1'}$ is a lower alkyl group or a lower alkoxyalkyl group, $R^{1''}$ is a lower alkyl group and n is an integer of 2 to 6; $R^2$ is a lower alkyl group, a lower cycloalkyl group or a lower alkoxyalkyl group and $R^3$ is a lower alkyl group, when X is nitrogen atom, $R^3$ is methyl group, or a pharmaceutically acceptable salt thereof, which comprises reacting 3-ethynylbenzaldehyde having the formula (II):

(II)

, an aminocrotonic acid derivative having the formula (III):

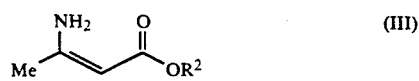

(III)

wherein $R^2$ is as defined above and a keto-ester or ketoamide derivative having the formula (IV):

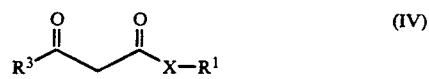

(IV)

wherein X, $R^1$ and $R^3$ are as defined above in an organic solvent, a process for preparing a 1,4-dihydropyridine derivative having the formula (I):

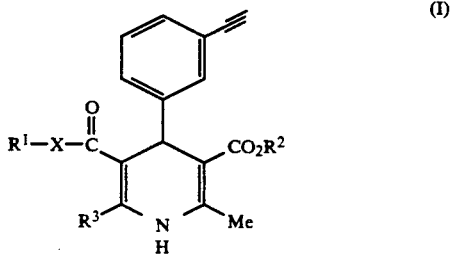

(I)

wherein X is oxygen atom, $R^1$ and $R^2$ are the same and each is a lower alkyl group or a lower cycloalkyl group and R³ is methyl group, or a pharmaceutically acceptable salt thereof, which comprises reacting 3-ethynylbenzaldehyde having the formula (II):

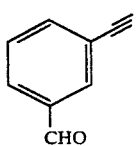
(II)

, a keto-ester derivative having the formula (IV'):

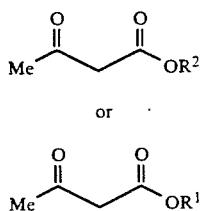
(IV')
or
(IV")

wherein R¹ and R² are as defined above and aqueous ammonia in a suitable organic solvent, a process for preparing a 1,4-dihydropyridine derivative having the formula (I):

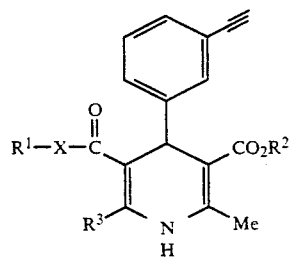
(I)

wherein X is oxygen atom or nitrogen atom; when X is oxygen atom, R¹ is a lower alkyl group, a lower cycloalkyl group or a lower alkenyl group, when X is nitrogen atom, X—R¹ group is $NH_2$, $NHR^{1'}$, $NR^{1'}R^{1''}$ or

in which $R^{1'}$ is a lower alkyl group or a lower alkoxyalkyl group, $R^{1''}$ is a lower alkyl group and n is an integer of 2 to 6; R² is a lower alkyl group, a lower cycloalkyl group or a lower alkoxyalkyl group and R³ is a lower alkyl group, formyl group, dimethoxymethyl group, cyano group or amino group, when X is nitrogen atom, R³ is methyl group, or a pharmaceutically acceptable salt thereof, which comprises reacting a benzylidene derivative having the formula (V):

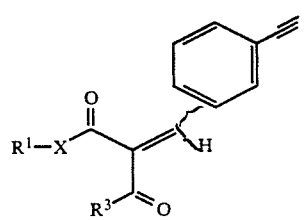
(V)

wherein X, R¹ and R³ are as defined above and an aminocrotonic acid derivative having the formula (III):

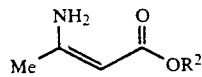
(III)

wherein R² is as defined above in a suitable organic solvent, a pharmaceutical composition for improving cerebral function which comprises as an effective ingredient the 1,4-dihydropyridine derivative (I) or a pharmaceutically acceptable salt thereof and a pharmaceutical composition for improving cerebral function which comprises an effective amount of the 1,4-dihydropyridine (I) or a pharmaceutically acceptable salt thereof and a pharmaceutically acceptable carrier.

BRIEF DESCRIPTION OF THE DRAWINGS

In FIG. 1 the compound No. 2 of the present invention is shown as closed circle and flunarizine is shown as open circle.

DETAILED DESCRIPTION

Figure 1:
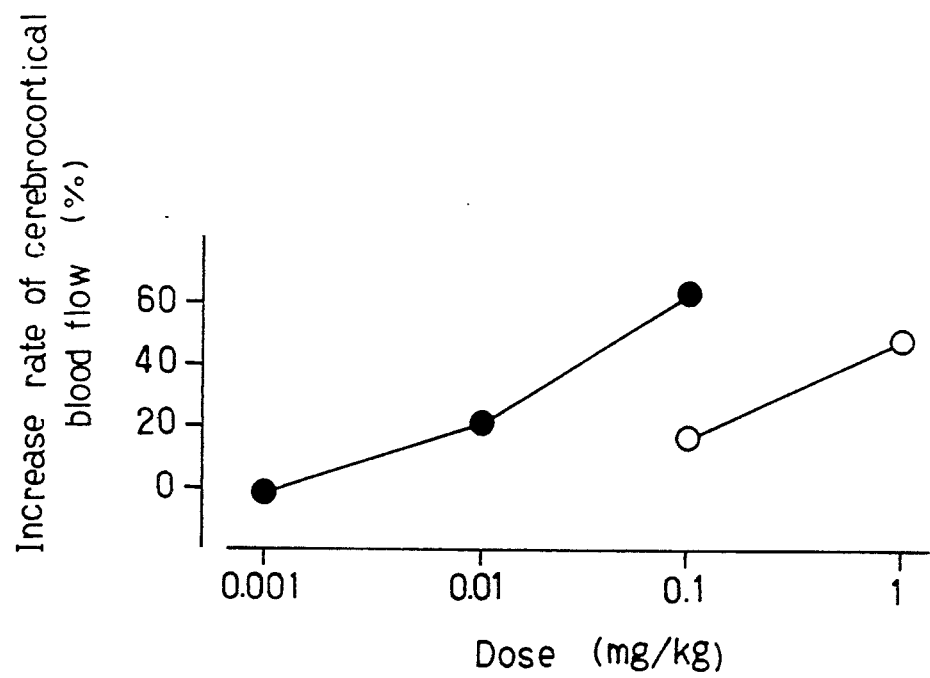
FIG. 1 is a graph showing relationship between each dose of the compound (I) of the present invention and flunarizine, and increase rate of cerebrocortical blood flow observed in Test Example 7 (activity for cerebral blood flow in rabbits).

The compound of the present invention is represented in the formula (I):

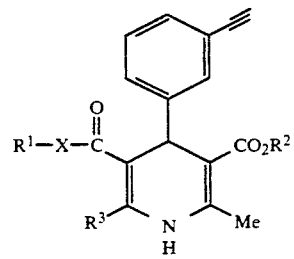
(I)

wherein X is oxygen atom or nitrogen atom; when X is oxygen atom, R¹ is hydrogen atom, a lower alkyl group, preferably a lower alkyl group consisting of a straight or branched chain having 1-4 carbon atoms, a lower cycloalkyl group, preferably a lower cycloalkyl group having 3-6 carbon atoms, a lower alkenyl group, preferably a lower alkenyl group consisting of a straight or branched chain having 3-5 carbon atoms, or magnesium atom, when X is nitrogen atom, X—R¹ group is $NH_2$, $NHR^{1'}$, $NR^{1'}R^{1''}$ or in which $R^{1'}$ is a lower alkyl group, preferably a lower alkyl group consisting of a straight or branched chain having 1-4 carbon atoms or a lower alkoxyalkyl group, preferably a lower alkoxyalkyl group having 1-2 carbon atoms, $R^{1''}$ is a lower alkyl group, preferably a lower alkyl group consisting of a straight or branched chain having 1-4 carbon atoms, and n is an integer of 2 to 6; R² is a lower alkyl group, preferably a lower alkyl group consisting of a straight or branched chain having 1-4 carbon atoms, a lower cycloalkyl group, preferably a lower cycloalkyl group having 3-6 carbon atoms or a lower alkoxyalkyl group, preferably a lower alkoxyalkyl group having 1-2 carbon atoms, and $R^3$ is a lower alkyl group, preferably a lower alkyl group consisting of a straight chain having 1-3 carbon atoms, formyl group, dimethoxymethyl group, cyano group or amino group, when X is oxygen atom and $R^1$ is hydrogen atom or magnesium atom, $R^3$ is methyl group, when X is nitrogen atom, $R^3$ is methyl group.

The compound having the formula (I) of the present invention can form a pharmaceutically acceptable salt with an acid as occasion demands. Examples of the salt with an acid are a salt with a mineral acid such as hydrochloric acid, hydrobromic acid, hydroiodic acid or sulfuric acid, a salt with an organic acid such as methanesulfonic acid, p-toluenesulfonic acid or benzenesulfonic acid and a salt with an organic acid such as acetic acid, phosphoric acid, oxalic acid, maleic acid, tartaric acid, citric acid, gluconic acid or lactic acid.

In many cases of the compounds having the formula (I) of the present invention, asymmetric carbons exist in the molecules thereof. The present invention includes these optical isomers and a mixture thereof.

As the compound having the formula (I) obtained according to the present invention, the compounds listed in Table 1 (in case that X is oxygen atom in the formula (I)) and Table 2 (in case that X is nitrogen atom in the formula (I)) can be exemplified.

TABLE 1

| Compound No. | $R^1X-$ | $R^2$ | $R^3$ |
| --- | --- | --- | --- |
| 1 | EtO*1 | Me | Me |
| 2 | EtO | Et | Me |
| 3 | MeO | Me*2 | Me |
| 4 | EtO | iPr | Me |
| 5 | n-PrO | Et | Me |
| 6 | iPrO | iPr*3 | Me |
| 7 | MeO | iPr | Me |
| 8 | MeO | nBu | Me |
| 9 | EtO | tBu | Me |
| 10 | tBuO | tBu*5 | Me |
| 11 | EtO | cyclopentyl | Me |
| 12 | HO | Et | Me |
| 13 | HO | iPr | Me |
| 14 | Mg½O | Me | Me |
| 15 | Mg½O | Et | Me |
| 16 | Mg½O | cyclohexyl | Me |
| 17 | Mg½O | iPr | Me |
| 18 | MeO | MeOCH$_2$— | Me |
| 19 | EtO | MeOCH$_2$— | Me |
| 20 | cyclohexyl-O | Et | Et |
| 21 | cyclohexyl-O | MeOCH$_2$CH$_2$— | Me |
| 22 | iPrO | MeOCH$_2$CH$_2$— | Me |
| 23 | MeO | Me | NH$_2$ |
| 24 | EtO | Et | NH$_2$ |
| 25 | EtO | Me | NH$_2$ |
| 26 | EtO | cyclohexyl | NH$_2$ |
| 27 | EtO | iPr | NH$_2$ |
| 28 | MeOCH$_2$CH$_2$O— | Me | NH$_2$ |
| 29 | MeO | Me | CN |
| 30 | EtO | Et | CN |
| 31 | EtO | Me | CN |
| 32 | iPrO | Me | CN |
| 33 | EtO | cyclohexyl | CN |
| 34 | MeOCH$_2$CH$_2$O— | Me | CN |
| 35 | MeOCH$_2$CH$_2$O— | cyclohexyl | CN |
| 36 | MeO | Me | CHO |
| 37 | EtO | Et | CHO |
| 38 | iPrO | Me | CHO |
| 39 | MeOCH$_2$CH$_2$O— | Me | CHO |
| 40 | MeO | Me | C(OMe)$_2$ |
| 41 | EtO | Et | C(OMe)$_2$ |
| 42 | MeOCH$_2$CH$_2$O— | Me | C(OMe)$_2$ |
| 49 | s-BuO*6 | Et | Me |
| 50 | CH$_2$=CHCH$_2$O— | Et | Me |
| 51 | CH$_3$CH=CHCH$_2$O— | Et | Me |

TABLE 1-continued

| Compound No. | $R^1X-$ | $R^2$ | $R^3$ |
| --- | --- | --- | --- |
| 52 | (CH$_3$)$_2$C=CHCH$_2$O— | Me | Me |

[Note]
*1: ethyl group
*2: methyl group
*3: isopropyl group
*4: n-butyl group
*5: t-butyl group
*6: s-butyl group

TABLE 2

| Compound No. | $XR^1$ | $R^2$ | $R^3$ |
| --- | --- | --- | --- |
| 43 | NH$_2$ | Me*1 | Me |
| 44 | NHMe | Me | Me |
| 45 | NHnBu | Et*2 | Me |
| 46 | N(iPr)$_2$*3 | Me | Me |
| 47 | piperidyl | Me | Me |
| 48 | NH$_2$ | cyclohexyl | Me |

[Note]
*1: methyl group
*2: ethyl group
*3: isopropyl group

The compound having the formula (I) of the present invention can be prepared by means of the following processes A-1, A-2, B, C-1, C-2, D-1, D-2, E, F, G and H.

Process A-1

The compound having the formula (I) wherein $R^3$ is a lower alkyl group can be prepared by Hantzsch synthesis method according to the reaction formula (a).

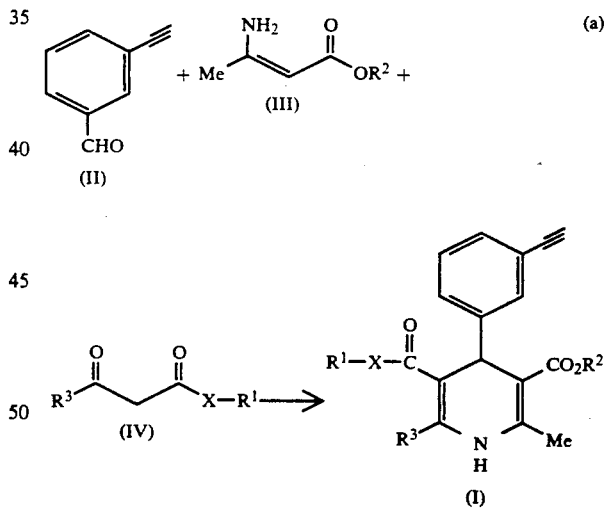

In the above-mentioned reaction formula (a), X is oxygen atom or nitrogen atom; when X is oxygen atom, $R^1$ is a lower alkyl group, a lower cycloalkyl group or a lower alkenyl group, when X is nitrogen atom, X—$R^1$ group is NH$_2$, NHR$^{1'}$, NR$^{1'}$R$^{1''}$ or

in which R$^{1'}$ is a lower alkyl group or a lower alkoxyalkyl group, R$^{1''}$ is a lower alkyl group and n is an integer of 2 to 6; $R^2$ is a lower alkyl group, a lower cycloalkyl group or a lower alkoxyalkyl group and $R^3$ is a lower alkyl group, when X is nitrogen atom, $R^3$ is methyl group.

In a typical process for preparation, the 1,4-dihydropyridine derivative having the formula (I) described in the reaction formula (a) can be prepared by adding 3-ethynylbenzaldehyde (II), an aminocrotonic acid derivative (III) and a keto-ester or keto-amide derivative (IV) to a suitable organic solvent such as a lower alkanol, e.g. ethanol.

Instead of the reaction formula (a), according to the reaction formula (b), the 1,4-dihydropyridine derivative (I) described in the reaction formula (a) can be prepared by adding 3-ethynylbenzaldehyde (II) and a keto-ester or keto-amide derivative (IV) in a solution of lower alkanol containing an aminocrotonic acid derivative (III) which is previously derived from a keto-ester derivative (IV') and ammonium carbonate or ammonium acetate.

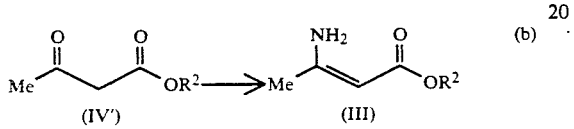

(b)

In the reaction formula (b), $R^2$ is as defined above, hereinafter "as defined above" means as described in the reaction formula (a).

With respect to the reaction formula (b), a solution of a lower alkanol which is prepared by adding a keto-ester derivative (IV') and 1 to 1.5 equivalents of ammonium carbonate or ammonium acetate per equivalent of keto-ester derivative (IV') to a lower alkanol is heated, typically for 30 minutes to 5 hours, preferably at 30° to 120° C. to substantially complete a conversion of the ketoester derivative (IV') into the aminocrotonic acid derivative (III).

Organic solvents which can be used in the present reaction are not particularly limited, if the solvents do not considerably inhibit this type of reaction. Examples of the suitable solvents are, for instance, lower alkanols such as ethanol, methanol, isopropyl alcohol and n-propyl alcohol.

With respect to the amount of each reactant in the present reaction, it is preferable that 1 to 1.5 equivalents of ammonium carbonate or ammonium acetate is used per equivalent of keto-ester derivative (IV').

In the present reaction, the reaction temperature is preferably from 30° to 120° C., and the reaction time is preferably 30 minutes to 5 hours.

The each amount of an aminocrotonic acid derivative (III) and a keto-ester or keto-amide derivative (IV) used in the reaction formula (a) is usually an equal equivalent or a little excess, preferably 1 to 1.3 equivalents per equivalent of 3-ethynylbenzaldehyde (II).

The obtained solution of a lower alkanol is stirred with heating for 1 to 24 hours, preferably at 20° to 200° C. until the reaction is substantially completed. Subsequently the compound having the formula (I) of the present invention obtained in the reaction formula (a) can be purified and isolated by means of a conventional treatment method, for instance, recrystallization, chromatography or the like.

That is, organic solvents which can be used in the present reaction are not particularly limited, if the solvents do not considerably inhibit this type of reaction. Examples of the suitable solvents are, for instance, lower alkanols such as ethanol, methanol, isopropyl alcohol and n-propyl alcohol.

With respect to the amount of each reactant in the present reaction, it is preferable that 1 to 1.3 equivalents of an aminocrotonic acid derivative (III) and of a keto-ester or keto-amide derivative (IV) are used per equivalent of 3-ethynylbenzaldehyde (II).

In the present reaction, the reaction temperature is preferably 20° to 120° C., and the reaction time is preferably 1 to 24 hours.

Process A-2

The compound having the formula (I) wherein $R^3$ is a lower alkyl group can be prepared according to the reaction formula (c).

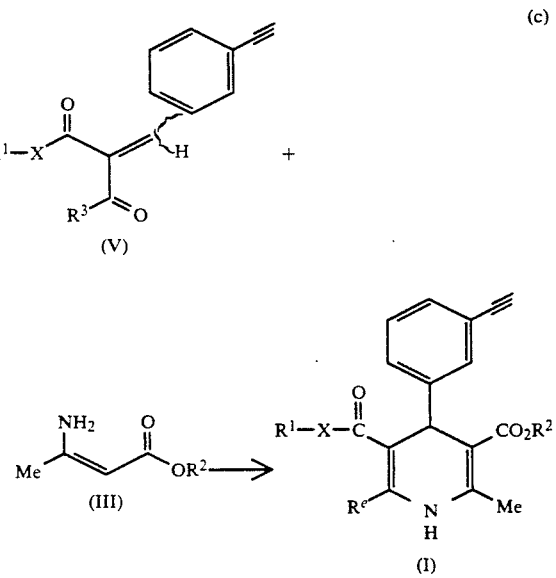

(c)

In the reaction formula (c), $R^3$ is a lower alkyl group and X, $R^1$ and $R^2$ are as defined above.

In a typical process for preparation, the 1,4-dihydropyridine derivative having the formula (I) described in the reaction formula (c) can be prepared by adding a benzylidene derivative (V) and an aminocrotonic acid derivative (III) to a suitable organic solvent such as a lower alkanol, e.g. ethanol. The amount of the aminocrotonic acid derivative (III) used in the reaction formula (c) is usually an equal equivalent or a little excess, preferably 1 to 1.3 equivalents per equivalent of benzylidene derivative (V).

The obtained solution of a lower alkanol is stirred with heating for 1 to 24 hours, preferably at 20° to 120° C. to substantially complete the reaction. Subsequently the compound having the formula (I) obtained in the reaction formula (c) can be purified and isolated according to a conventional method, for instance, recrystallization, chromatography or the like.

That is, organic solvents which can be used in the present reaction, if the solvents do not considerably inhibit this type of reaction. Examples of the suitable solvents are, for instance, lower alkanols such as ethanol, methanol, isopropyl alcohol and n-propyl alcohol.

With respect to the amount of each reactant in the present reaction, it is preferable that 1 to 1.3 equivalents of an aminocrotonic acid derivative (III) is used per equivalent of benzylidene derivative (V).

In the present reaction, the reaction temperature is preferably 20° to 120° C., and the reaction time is preferably 1 to 24 hours.

The benzylidene derivative (V) used in the reaction formula (c) can be prepared according to the reaction formula (d).

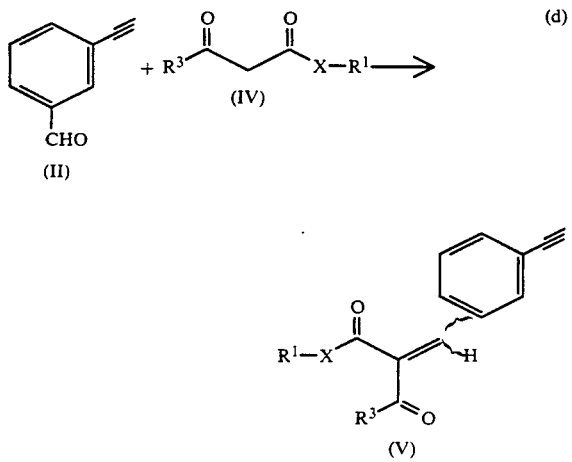

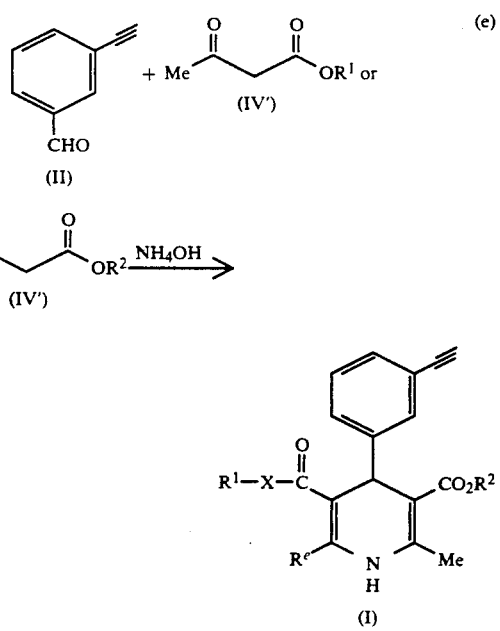

In the reaction formula (d), R³ is a lower alkyl group, and X and R¹ are as defined above.

In a typical process for preparation, an equal equivalent of 3-ethynylbenzaldehyde (II) and a keto-ester or keto-amide derivative (IV) are added to a suitable aromatic organic solvent such as toluene or benzene, and the mixture is reacted with using a suitable amine such as a cyclic secondary amine, e.g. piperidine, pyrrolidine or the like or a lower tertiary alkylamine, e.g. a triethylamine or the like as a base catalyst. The reaction solution is usually refluxed, and produced water is removed by a Dean Stark trap. The reaction solution is stirred with heating for 2 to 24 hours, preferably at 20° to 120° C. to substantially complete the reaction.

The isolation and purification of the compound having the formula (V) are carried out according to the method previously explained in Process A-1.

That is, organic solvents which can be used in the present reaction, if the solvents do not considerably inhibit this type of reaction. Examples of the suitable solvents are, for instance, aromatic organic solvents such as toluene, benzene and xylene.

With respect to the amount of each reactant in the present reaction, it is preferable that 1 to 1.3 equivalents of a keto-ester or keto-amide derivative (IV) is used per equivalent of 3-ethynylbenzaldehyde (II).

In the present reaction, the reaction temperature is preferably 20° to 120° C., and the reaction time is preferably 2 to 24 hours.

Process B

The compound having the formula (I) described in the reaction formula (e) wherein X is oxygen atom, R³ is methyl group, R¹ and R² are the same and each is a lower alkyl group or a lower cycloalkyl group can be prepared by Hantzsch synthesis method according to the reaction formula (e).

In the reaction formula (e), X is oxygen atom, R¹ and R² are the same and each is a lower alkyl group or a lower cycloalkyl group and R³ is methyl group.

In a typical process for preparation, the 1,4-dihydropyridine derivative having the formula (I) described in the reaction formula (e) can be prepared by adding 3-ethynylbenzaldehyde (II) and a keto-ester derivative (IV') and aqueous ammonia to a suitable organic solvent such as a lower alkanol, e.g. ethanol. The amount of the keto-ester derivative (IV') used in the present reaction is usually an equal equivalent or a little excess, preferably 1 to 1.3 equivalents per equivalent of 3-ethynylbenzaldehyde (II). The concentration of aqueous ammonia used in the present reaction is not limited, but a 10 to 28% by weight (hereinafter the same) aqueous solution of ammonia is preferably used. The amount of the aqueous ammonia used in the present reaction is usually a large excess, preferably 2 to 5 equivalents per equivalent of 3-ethynylbenzaldehyde (II). The obtained solution of a lower alkanol is stirred with heating for 1 to 24 hours, preferably at 20° to 120° C. to substantially complete the reaction. Subsequently the purification and isolation of the compound having the formula (I) obtained in the reaction formula (e) are carried out according to the method previously explained in Process A-1.

That is, organic solvents which can be used in the present reaction are not limited, if the solvents do not considerably inhibit this type of reaction. Examples of the suitable solvents are lower alkanols such as ethanol, methanol, isopropyl alcohol, n-propyl alcohol and the like.

With respect to the amount of each reactant in the present reaction, it is preferable that 1 to 1.3 equivalents of a keto-ester derivative (IV') is used per equivalent of 3-ethynylbenzaldehyde (II).

In the present reaction, the reaction temperature is preferably 20° to 120° C., and the reaction time is preferably 1 to 24 hours.

Process C-1

The compound having the formula (I) wherein X is oxygen atom and R³ is amino group can be prepared according to the reaction formula (f).

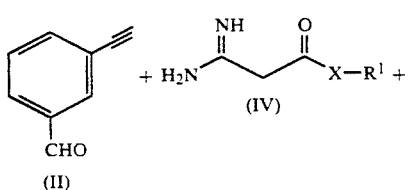
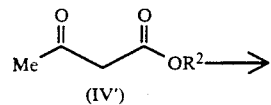
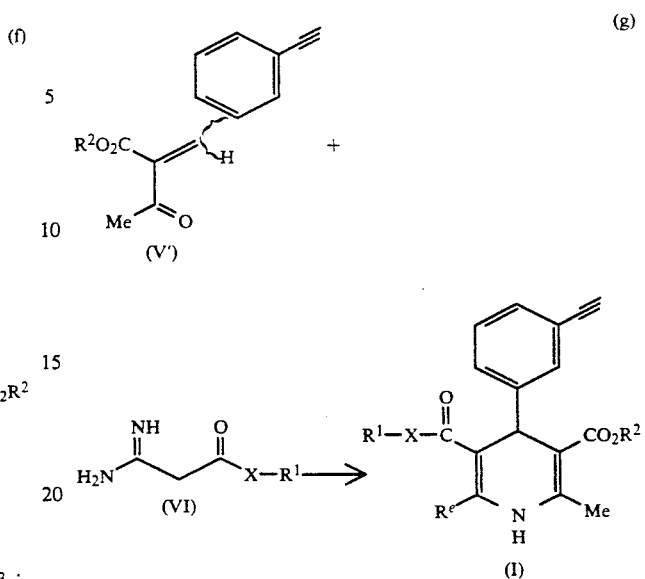

In the reaction formula (f), X is oxygen atom, $R^3$ is amino group, $R^1$ and $R^2$ are as defined above.

In a typical process for preparation, the 1,4-dihydropyridine derivative having the formula (I) described in the reaction formula (f) can be prepared by adding 3-ethynylbenzaldehyde (II), an amidine derivative (VI) and a keto-ester derivative (IV') to a suitable organic solvent such as a lower alkanol, e.g. ethanol.

The amount of the amidine derivative (VI) and the keto-ester derivative (IV') used in the present reaction is usually an equal equivalent or a little excess, preferably 1 to 1.3 equivalents per equivalent of 3-ethynylbenzaldehyde (II). The obtained solution of a lower alkanol is stirred with heating for 1 to 24 hours, preferably at 20° to 120° C. to substantially complete the reaction. Subsequently the purification and isolation of the compound having the formula (I) obtained in the reaction formula (f) are carried out according to the method previously explained in Process A-1.

That is, organic solvents which can be used in the present reaction are not limited if the solvents do not considerably inhibit this type of reaction. Examples of the suitable solvents are lower alkanols such as ethanol, methanol, isopropyl alcohol, n-propyl alcohol and the like.

With respect to the amount of each reactant in the present reaction, it is preferable that 1 to 1.3 equivalents of an amidine derivative (IV) and of a ketoester derivative (IV') are used per equivalent of 3-ethynylbenzaldehyde (II).

In the present reaction, the reaction temperature is preferably 20° to 120° C., and the reaction time is preferably 1 to 24 hours.

Process C-2

The compound having the formula (I) wherein X is oxygen atom and $R^3$ is amino group can be prepared according to the reaction formula (g).

In the reaction formula (g), X is oxygen atom, $R^3$ are amino group, $R^1$ and $R^2$ are as defined above.

The benzylidene derivative (V') used in the present reaction can be prepared from 3-ethynylbenzaldehyde (II) and a keto-ester derivative (IV') according to the reaction formula (d') in the same manner as explained in Process A-2.

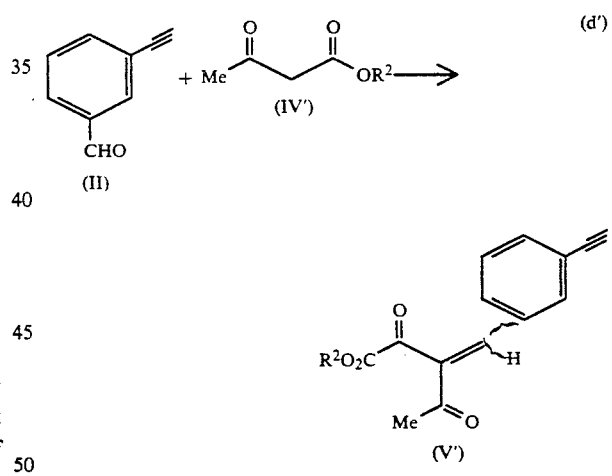

In the reaction formula (d'), $R^2$ is as defined above.

In a typical process for preparation, the 1,4-dihydropyridine derivative having the formula (I) described in the reaction formula (g) can be prepared by adding a benzylidene derivative (V') and an amidine derivative (VI) to a suitable organic solvent such as a lower alkanol, e.g. ethanol. The amount of the amidine derivative (VI) used in the present reaction is usually an equal equivalent or a little excess, preferably 1 to 1.3 equivalents per equivalent of benzylidene derivative (V'). The obtained solution of a lower alkanol is stirred with heating for 1 to 24 hours, preferably at 20° to 120° C. to substantially complete the reaction. Subsequently the purification and isolation of the compound having the formula (I) obtained in the reaction formula (g), are carried out according to the method previously explained in Process A-1.

That is, organic solvents which can be used in the present reaction are not limited, if the solvents do not considerably inhibit this type of reaction. Examples of the suitable solvents are lower alkanols such as ethanol, methanol, isopropyl alcohol, n-propyl alcohol and the like.

With respect to the amount of each reactant in the present reaction, it is preferable that 1 to 1.3 equivalents of the amidine derivative (VI) is used per equivalent of benzylidene derivative (V').

In the present reaction, the reaction temperature is preferably 20° to 120° C., and the reaction time is preferably 1 to 24 hours.

Process D-1

The compound having the formula (I) wherein X is oxygen atom and $R^3$ is dimethoxymethyl group can be prepared according to the reaction formula (h).

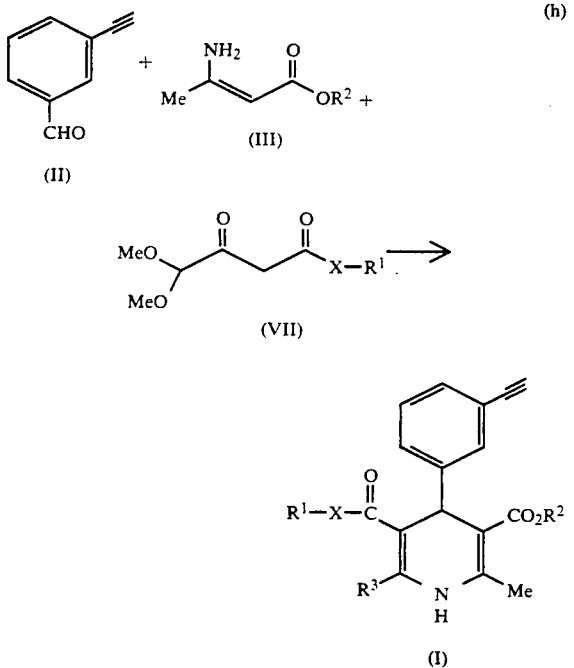

In the reaction formula (h), X is oxygen atom, $R^3$ is dimethoxymethyl group, $R^1$ and $R^2$ are as defined above.

In a typical process for preparation, the 1,4-dihydropyridine derivative having the formula (I) described in the reaction formula (h) can be prepared by adding 3-ethynylbenzaldehyde (II), an aminocrotonic acid derivative (III) and an acetal keto-ester derivative (VII) to a suitable organic solvent such as a lower alkanol, e.g. ethanol.

Instead of the reaction formula (h), according to the reaction formula (b), the 1,4-dihydropyridine derivative (I) described in the reaction formula (h) can be prepared by adding 3-ethynylbenzaldehyde (II) and an acetal keto-ester derivative (VII) to a solution of a lower alkanol containing an aminocrotonic acid derivative (III) which is previously derived from a keto-ester derivative (IV') as explained in Process A-1. The amount of the aminocrotonic acid derivative (III) and the acetal keto-ester derivative (VII) used in the present reaction is usually an equal equivalent or a little excess, preferably 1 to 1.3 equivalents per equivalent of 3-ethynylbenzaldehyde (II).

The obtained solution of a lower alkanol is stirred with heating for 1 to 24 hours, preferably at 20° to 120° C. to substantially complete the reaction. Subsequently the purification and isolation of the compound having the formula (I) obtained in the reaction formula (h) are carried out according to the method previously explained in Process A-1.

That is, organic solvents which can be used in the present reaction are not limited, if the solvents do not considerably inhibit this type of reaction. Examples of the suitable solvent are lower alkanols such as ethanol, methanol, isopropyl alcohol, n-propyl alcohol and the like.

With respect to the amount of each reactant in the present reaction, it is preferable that 1 to 1.3 equivalents of an aminocrotonic acid derivative (III) and an acetal keto-ester derivative (VII) is used per equivalent of 3-ethynylbenzaldehyde (II).

In the present reaction, reaction temperature is preferably 20° to 120° C., and the reaction time is preferably 1 to 24 hours.

Process D-2

The compound having the formula (I) wherein X is oxygen atom and $R^3$ is dimethoxymethyl group can be prepared according to the reaction formula (i).

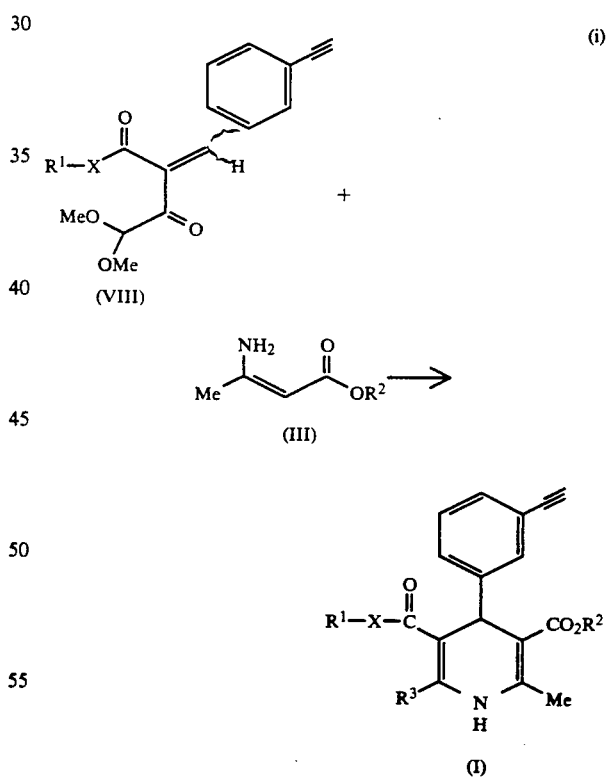

In the reaction formula (i), X is oxygen atom, $R^3$ is dimethoxymethyl group, $R^1$ and $R^2$ are as defined above.

The benzylidene derivative (VIII) used in the present reaction can be prepared from 3-ethynylbenzaldehyde (II) and an acetal keto-ester derivative (VII) in the same manner as explained in Process A-2 according to the reaction formula (d'').

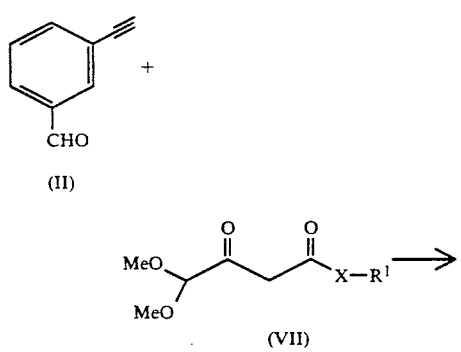

(II)

(VII)

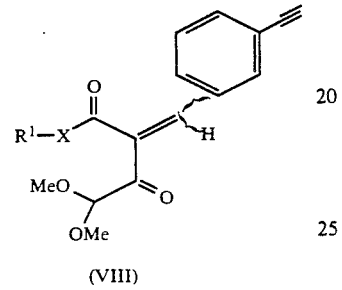

(VIII)

In the reaction formula (d"), X is oxygen atom and $R^1$ is as defined above.

In a typical process for preparation, the 1,4-dihydropyridine derivative having the formula (I) described in the reaction formula (i) can be prepared by adding a benzylidene derivative (VIII) and an aminocrotonic acid derivative (III) to a suitable organic solvent such as a lower alkanol, e.g. ethanol. The amount of the aminocrotonic acid derivative (III) used in the present reaction is usually an equal equivalent or a little excess, preferably 1 to 1.3 equivalents per equivalent of benzylidene derivative (VIII). The obtained mixture solution of a lower alkanol is stirred with heating for 1 to 24 hours, preferably 20° to 120° C. to substantially complete the reaction. Subsequently the purification and isolation of the compound having the formula (I) obtained the reaction formula (d") are carried out according to the method previously explained in Process A-1.

That is, organic solvents which can be used in the present reaction are not limited, if the solvents do not considerably inhibit this type of reaction. Examples of the suitable solvents are lower alkanols such as ethanol, methanol, isopropyl alcohol, n-propyl alcohol and the like.

With respect to the amount of each reactant in the present reaction, it is preferable that 1 to 1.3 equivalents of an aminocrotonic acid derivative (III) is used per equivalent of benzylidene derivative (VIII).

In the present reaction, the reaction temperature is preferably 20° to 120° C., and the reaction time is preferably 1 to 24 hours.

Process E

The compound having the formula (I) wherein X is oxygen atom and $R^3$ is formyl group can be prepared by hydrolysis of the compound having the formula (I) wherein $R^3$ is dimethoxymethyl group, which can be prepared by the process explained in Processes D-1 and D-2 according to the reaction formula (j).

(I) (X = O, $R^3$ = CH(OMe)$_2$)

(I) (X = O, $R^3$ = CHO)

In the reaction formula (j), $R^1$ and $R^2$ are as described in the reaction formula (a).

In a typical process for preparation, the 1,4-dihydropyridine derivative having the formula (I) described in the reaction formula (j) wherein X is O and $R^3$ is CHO can be prepared by adding the 1,4-dihydropyridine derivative (I) wherein X is O and $R^3$ is CH(OMe)$_2$ described in the reaction formula (j) to a suitable organic solvent such as acetone, dioxane, tetrahydrofuran, dimethylsulfoxide, N,N-dimethylformamide and water, or an admixture thereof and sequentially adding an acid, for instance, an inorganic acid such as hydrochloric acid, sulfuric acid or the like, an organic acid such as acetic acid, formic acid, trifluoroacetic acid, p-toluene sulfonic acid or the like, or an acidic ion exchange resin or the like.

The amount of the acid used in the present reaction is usually so called catalytic amount, preferably 0.01 to 0.05 equivalent per equivalent of the 1,4-dihydropyridine derivative (I) wherein X is O and $R^3$ is CH(OMe)$_2$. The obtained reaction mixture is stirred with heating for 1 to 12 hours, preferably at 0° to 60° C. to substantially complete the reaction. Subsequently the purification and isolation of the compound having the formula (I) described in the reaction formula (j) wherein X is O and $R^3$ is CHO, are carried out according to the method previously explained in Process A-1.

That is, in the present reaction, the reaction temperature is preferably 0° to 60° C., and the reaction time is preferably 1 to 12 hours.

Process F

The compound having the formula (I) described in the reaction formula (k) wherein X is oxygen atom and $R^3$ is cyano group can be prepared by converting the compound having the formula (I) described in the reaction formula (j) wherein X is O and $R^3$ is CHO into an oxime and subsequently by dehydration reaction.

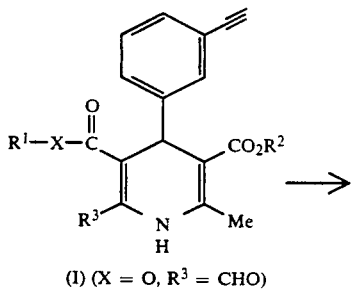

(I) (X = O, R³ = CHO)

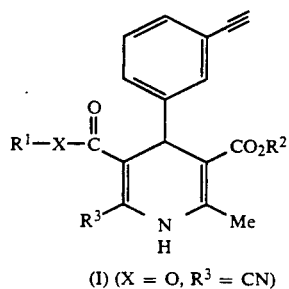

(I) (X = O, R³ = CN)

In the reaction formula (k), R¹ and R² are as described in the reaction formula (a).

As the typical preparation processes, the following process is exemplified. The 1,4-dihydropyridine derivative having the formula (I) wherein X is O and R³ is CHO, which is described in the reaction formula (j), and hydroxylamine or its salt (for instance, a salt of an inorganic acid such as hydrochloric acid or sulfuric acid, a salt of an organic acid such as acetic acid or formic acid, or the like) is added to a suitable organic solvent such as dioxane, ethanol, N,N-dimethylformamide, water or an admixture thereof. Then, an acid and/or an inorganic weak base is added to the mixture. Examples of the acids are, for instance, an inorganic acid such as hydrochloric acid, hydrobromic acid or sulfuric acid, an organic acid such as acetic acid, formic acid, trifluoroacetic acid or p-toluenesulfonic acid, and the like. Examples of the inorganic weak base are, for instance, sodium acetate, potassium acetate, sodium formate, and the like. Hydroxylamine or its salt is used in an amount, generally, of an equal equivalent or a little excess preferably from 1 to 1.3 equivalents per equivalent of the 1,4-dihydropyridine derivative having the formula (I) wherein X is O and R³ is CHO. The amount of the acid is from 20 to 50 equivalents per equivalent of the used 1,4-dihydropyridine derivative having the formula (I) wherein X is O and R³ is CHO. When the acid is in the state of a liquid, the acid is used as the solvent. The amount of the inorganic weak base is generally from 1 to 1.5 equivalents per equivalent of the used hydroxylamine or its salt. Thus mixture is stirred until the reaction is substantially completed, for 1 to 5 hours, preferably at a temperature of 0° to 50° C.

That is to say, in the conversion of the 1,4-dihydropyridine derivative into an oxime, it is preferable that hydroxylamine is used in an amount of 1 to 1.3 equivalents per equivalent of the 1,4-dihydropyridine derivative having the formula (I) wherein X is O and R³ is CHO, which is described in the reaction formula (j), the acid is used in an amount of 20 to 50 equivalents per equivalent of the 1,4-dihydropyridine derivative, and if necessary, the inorganic weak base is used in an amount of 1 to 1.5 equivalents per equivalent of the hydroxylamine or its salt.

In the conversion into an oxime as mentioned above, it is preferable that the reaction temperature is from 0° to 50° C. and reaction time is from 1 to 5 hours.

The thus prepared oxime is isolated from the reaction mixture and is purified, then is subjected to dehydration, or the obtained reaction mixture is subjected to dehydration as it is. In case of isolating, the same solvent as used in conversion into an oxime is usually used in dehydration. Subsequently, a dehydrating agent is added to the solution containing the oxime as an intermediate. Examples of the dehydrating agents are, for instance, an inorganic acid such as sulfuric acid, phosphoric acid or polyphosphoric acid, an organic acid such as formic acid, acetic acid or p-toluenesulfonic acid, an organic acid anhydride such as benzoic anhydride, acetic anhydride or phthalic anhydride, an organic acid chloride such as acetyl chloride, benzoyl chloride, methanesulfonic acid chloride or formyl chloride, an inorganic chloride such as thionyl chloride, phosphorus pentachloride, phosphorus oxychloride or phosphorus tribromide, a carbodiimide such as N,N'-dicyclohexylcarbodiimide, and the like. The amount of the used dehydrating agent generally exceeds the amount of the 1,4-dihydropyridine derivative having the formula (I) wherein X is O and R³ is CHO. It is preferable that the dehydrating agent is used in an amount of 3 to 7 equivalents per equivalent of the 1,4-dihydropyridine derivative (I) wherein X is O and R³ is CHO. The mixture is stirred until the dehydration is substantially completed, for 1 to 10 hours, preferably at a temperature of 20° to 130° C. The obtained 1,4-dihydropyridine derivative having the formula (I) wherein X is O and R³ is CN is isolated and purified in the same manner as in Process A-1.

That is, in dehydration of Process F, it is preferable to use the dehydrating agent in an amount of 3 to 7 equivalents per equivalent of the 1,4-dihydropyridine derivative having the formula (I) wherein X is O and R³ is CHO.

It is preferable that the dehydration is carried out at a temperature of 20° to 130° C. for 1 to 10 hours.

Process G

The compound having the formula (I) wherein X is oxygen atom, R¹ is hydrogen atom and R³ is methyl group can be obtained by hydrolysis reaction, according to the reaction formula (l).

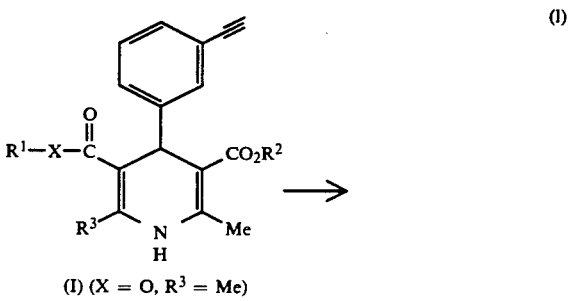

(I) (X = O, R³ = Me)

-continued

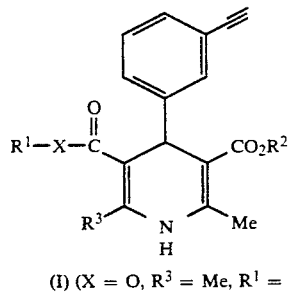

(I) (X = O, R³ = Me, R¹ = H)

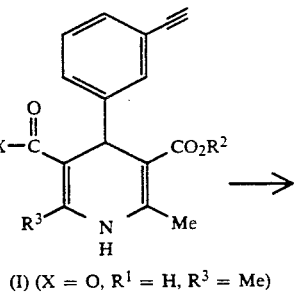

(I) (X = O, R¹ = H, R³ = Me)

In the above mentioned reaction formula (1), there is preferable, as a raw material, a 1,4-dihydropyridine derivative having the formula (I) wherein $R^1$ and $R^2$ are the same. In the 1,4-dihydropyridine derivative (I) being a starting compound in the reaction formula (1), $R^1$ and $R^2$ as defined above.

As a typical process, the following process is exemplified. That is, the 1,4-dihydropyridine derivative having the formula (I) wherein X is O and $R^3$ is methyl group, which is described in the reaction formula (1), is added to a suitable organic solvent, for instance, a lower alkanol such as ethanol, then an aqueous solution of an inorganic base such as sodium hydroxide or potassium hydroxide is added to the mixture to give the 1,4-dihydropyridine derivative having the formula (I) wherein X is O, $R^3$ is methyl group and $R^1$ is hydrogen atom. The inorganic base is used in an amount of, generally an equal equivalent or a little excess, preferably 1 to 2.5 equivalents per equivalent of the 1,4-dihydropyridine derivative having the formula (I) wherein X is O and $R^3$ is methyl group. It is preferable that the alkali solution to be added is adjusted to a concentration of 0.1 to 1N. The thus prepared lower alkanol solution is stirred with heating until the reaction is substantially completed, for 10 to 96 hours, preferably at 20° to 60° C. The reaction condition is not limited thereto. The obtained 1,4-dihydropyridine derivative having the formula (I) wherein X is O, $R^1$ is hydrogen atom and $R^3$ is methyl group is isolated and purified in the same manner as in Process A-1.

The organic solvent used in the present reaction is not particularly limited so long as the hydrolysis reaction is not remarkably inhibited. A lower alkanol such as ethanol, methanol, isopropyl alcohol or n-propyl alcohol is preferable.

It is preferable that the amount of the inorganic base used in the reaction is 1 to 2.5 equivalents per equivalent of the 1,4-dihydropyridine derivative having the formula (I) wherein X is O and $R^3$ is methyl group.

It is preferable that the reaction temperature is from 20° to 60° C. and the reaction time is from 10 to 96 hours.

Process H

The 1,4-dihydropyridine derivative having the formula (I) wherein X is oxygen atom, $R^1$ is magnesium atom, $R^3$ is methyl group and $R^2$ is as defined above can be obtained by neutralizing the 1,4-dihydropyridine derivative having the formula (I) wherein X is O, $R^1$ is hydrogen atom, $R^3$ is methyl group and $R^2$ is as defined above with a magnesium alkoxide according to the reaction formula (m):

(m)

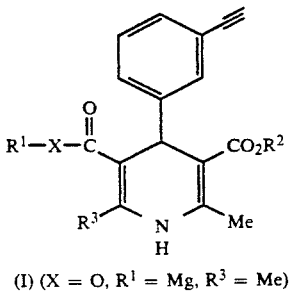

(I) (X = O, R¹ = Mg, R³ = Me)

In the reaction formula (m), $R^2$ is as defined above.

The typical preparation process is as follows:

The 1,4-dihydropyridine derivative having the formula (I) wherein X is O, $R^1$ is hydrogen atom and $R^3$ is methyl group, which is described in the reaction formula (m) is dissolved in a lower alkanol such as anhydrous methanol or anhydrous ethanol, and the obtained solution is added to a lower alkanol solution of magnesium alkoxide such as magnesium methoxide or magnesium ethoxide which is previously prepared by using magnesium in an amount of an equal equivalent to the 1,4-dihydropyridine derivative (I) wherein X is O, $R^1$ is hydrogen atom and $R^3$ is methyl. Thus obtained mixture is stirred for 0.5 to 5 hours at a temperature, generally, of 20° to 80° C. Then, the solvent is distilled away from the reaction mixture to give the magnesium salt of the 1,4-dihydropyridine derivative having the formula (I) wherein X is O, $R^1$ is magnesium atom and $R^3$ is methyl group. It is preferable that the reaction temperature is from 20° to 80° C. and the reaction time is from 0.5 to 5 hours.

The aminocrotonic acid derivative (III), the keto-ester or keto-amide derivative (IV), the amidine derivative (VI) and the acetal keto-ester derivative (VII) which are the raw material compounds used in Processes A-1 to H are prepared as follows: Preparation process of the aminocrotonic acid derivative (III)

A keto-ester derivative such as a compound having the formula (IV') wherein $R^2$ is as defined above is treated with liquid ammonia according to the following reaction formula (n) to give the aminocrotonic acid derivative (III).

(n)

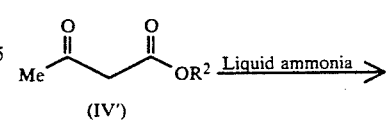

(IV')

-continued

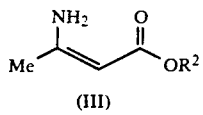
(III)

In the reaction formula (n), $R^2$ is as defined above. Preparation process of the keto-ester or keto-amide derivative (IV)

An alcohol or amine (IX) is reacted with a diketene (X) in the presence of a basic catalyst to give a keto-ester or keto-amide derivative (IV'') wherein $R^3$ is methyl group, further in case of the compound (IV'') wherein X is oxygen atom, the obtained compound (IV'') is reacted with a suitable electrophilic reagent by a method described in Organic Reaction, 17, page 155 (1969), according to the reaction formula (o) to give the ketoester or keto-amide derivative (IV) wherein X, $R^1$ and $R^3$ are as defined above.

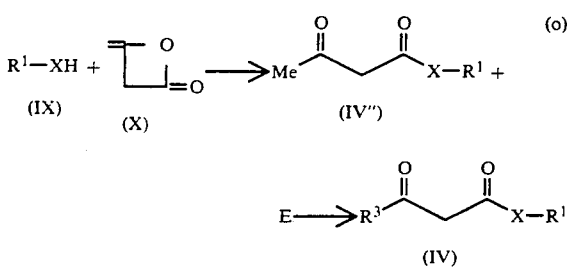

In the reaction formula (o), X, $R^1$ and $R^3$ is as defined above.

Preparation process of the amidine derivative (VI)

A cyanomalonic acid ester derivative (XI) is treated with hydrogen chloride in a lower alkanol such as ethanol to give an imidate derivative (XII) wherein R is a lower alkyl group having 1 to 3 carbon atoms [See S. A. Glickman and A. C. Cope, Journal of the American Chemical Society, 67, page 1017 (1945)], then the obtained compound (XII) is treated with liquid ammonia according to the reaction formula (p) to give the amidine derivative (VI) [see S. M. McElvain and B. E. Tate, Journal of the American Chemical Society, 73, page 2760 (1951)].

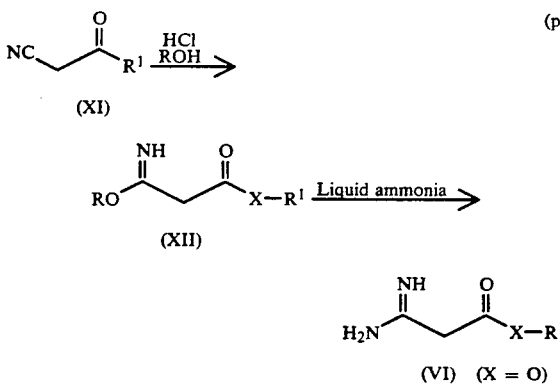

In the reaction formula (p), R is a lower alkyl group having 1 to 3 carbon atoms, X is oxygen atom and $R^1$ is as defined above.

Preparation process of the acetal keto-ester derivative (VII)

Pyruvic aldehyde dimethyl acetal (XIII) is condensed with a lower alcohol ester of carbonic acid according to following the reaction formula (q) to give the acetal keto-ester derivative (VII) wherein X is oxygen atom and $R^1$ is as defined above [see J. A. Secrist, C. J. Hickey and R. E. Norris, Journal of Organic Chemistry, 42, page 525 (1977)].

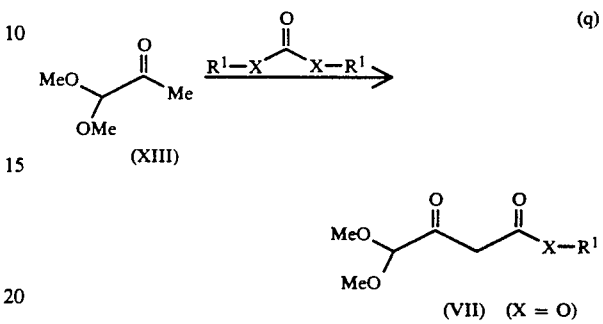

In the reaction formula (q), X is oxygen atom and $R^1$ is as defined above.

The reagents and reaction conditions used in the preparation processes of the raw material compounds as mentioned above are used those well known in the art.

The 1,4-dihydropyridine derivative having the formula (I) have cerebroprotective activity, cerebroactivating activity and cerebrocirculation improvement activity, and is low in toxicity. Therefore, the derivative (I) is useful as an effective component of the cerebral function improver.

Among the 1,4-dihydropyridine derivatives having the formula (I), there are preferable the compounds having the formula (I) wherein X is oxygen atom or nitrogen atom, the compounds having the formula (I) wherein each $R^1$, $R^2$ and $R^3$ is the lower alkyl group, the compounds having the formula (I) wherein $R^3$ is amino group, the compounds having the formula (I) wherein $R^3$ is cyano group, the compounds having the formula (I) wherein $R^3$ is formyl group, the compounds having the formula (I) wherein $R^3$ is dimethoxymethyl group, the compounds having the formula (I) wherein $R^1$ is hydrogen atom or magnesium atom and X is oxygen atom, the compounds having the formula (I) wherein $R^1$ and $R^2$ are independently the alkyl groups, the compounds having the formula (I) wherein $R^1$ is the lower cycloalkyl group, the compounds having the formula (I) wherein $R^1$ is the lower alkoxyalkyl group, the compounds having the formula (I) wherein $R^2$ is the lower alkyl group and the compounds having the formula (I) wherein $R^2$ is the lower cycloalkyl group.

The compound having the formula (I) of the present invention as an effective ingredient may be in any preparation form for oral or parenteral administration. Examples of the preparation form are, for instance, preparations for oral administration such as tablets, capsules, granules, powders, syrups, preparations for parenteral administration such as injections containing subcutaneous injection and intravenous injection, suppositories, cataplasmata, emplastra and the like. These preparations of the pharmaceutical composition of the present invention are can be prepared in a usual method by using any conventional carriers which is pharmaceutically accepted in the basis in accordance with the purpose. Examples of the carrier include gelatin, lactose, sucrose, titanium oxide, starch, crystalline cellulose, hydroxypropylmethyl cellulose, carboxymethyl cellulose, corn starch, microcrystalline wax, white petrolatum, magnesium alumino meta silicate, anhydrous calcium phosphate, citric acid, trisodium citrate, hydroxypropyl cellulose, sorbitol, sorbitan esters of fatty acids, polyvinylpyrrolidone, magnesium stearate, light anhydrous silicic acid, talc, vegetable oil, benzyl alcohol, gum arabic, propylene glycol or polyalkylene glycol. The content of the compound having the formula (I) of the present invention in the preparation varies from 1 to 50% by weight. The pharmaceutical composition of the present invention can contain another pharmaceutical ingredient such as another cerebral function improver compatible with the compound (I) of the present invention. In this case, the compound of the present invention is not necessarily a main ingredient of the preparation.

Although the dosage of the compound of the present invention is different according to sympton, age, body weight, route, times and period of administration, a usual dose is about 2 to 300 mg, on the basis of the compound (I) of the present invention per day for adults, and can be devided to 1 to several times.

The 1,4-dihydropyridine derivative (I) of the present invention was examined as to activity against maximal electroshock-induced seizures in mice (Test Example 1), activity against immobility time of forced swimming test in mice (Test Example 2), activity against convulsion induced by pentylentetrazole (Test Example 3), activity against blood pressure (Test Example 4), activity against decapitation induced hypoxia in mice (Test Example 5), acute toxicity in mice (Test Example 6) and activity against cerebrocortical blood flow in rabbits (Test Example 7).

The present invention is more specifically described and explained by means of the following Test Examples, Examples and Formulation Examples in which all percents and parts are by weight unless otherwise noted. It is to be understood that the present invention is not limited to the Test Examples, the Examples and the Formulation Examples, and various changes and modifications may be made in the invention without departing from the spirit and scope thereof.

TEST EXAMPLE 1

Activity against maximal electroshock-induced seizures

In each group six Slc: ddy male mice weighing 26 to 31 g (5 weeks) were employed. Sixty minutes after oral administration of a test compound, corneal electrodes which were wet by physiological saline were contacted with both eyes of a mouse. Then, appearance of tonic extensive convulsion (TE) caused by electrifying under a stimulation condition of 50 mA, 1000 V and 0.2 sec by means of the apparatus of Woodburg & Davenport (made by Kyoto Keisokuki) was judged as indication.

Each of diphenylhydantoin, the compounds Nos. 2, 4, 5, 6, 7, 50, 51 and 52 of the present invention (refer Table 1, hereinafter the same) and nimodipine was suspended in a 0.5% solution of methyl cellulose to subject the test. Flunarizine was suspended in a 5% solution of gum arabic to subject the test.

The results are shown in Table 3.

TABLE 3

| Test compound | Dose (mg/kg, oral administration) | Number of appearance of tonic extensive convulsion |
| --- | --- | --- |
| Control (0.5% methyl cellulose) | — | 6 cases/6 cases |
| Compound No. 2 (Example 2) | 50 | 6 cases/6 cases |
|  | 100 | 2 cases/6 cases |
|  | 200 | no case/6 cases |
| Compound No. 4 (Example 24) | 50 | 2 cases/6 cases |
|  | 100 | 1 case/6 cases |
| Compound No. 5 (Example 25) | 200 | 2 cases/6 cases |
| Compound No. 6 (Example 4) | 200 | 4 cases/6 cases |
| Compound No. 7 (Example 26) | 200 | 4 cases/6 cases |
| Compound No. 50 (Example 28) | 200 | no case/6 cases |
| Compound No. 51 (Example 29) | 200 | no case/6 cases |
| Compound No. 52 (Example 30) | 200 | 2 cases/6 cases |
| Diphenylhydantoin | 25 | 1 case/6 cases |
|  | 100 | no case/6 cases |
|  | 200 | no case/6 cases |
| Nimodipine | 50 | 6 cases/6 cases |
|  | 100 | 6 cases/6 cases |
|  | 200 | 6 cases/6 cases |
| Control (5% gum arabic) | — | 6 cases/6 cases |
| Flunarizine | 50 | 6 cases/6 cases |
|  | 100 | 4 cases/6 cases |
|  | 200 | 1 case/6 cases |

As shown in Table 3, inhibitory activity against tonic extensive convulsion was observed in two thirds case of the administration of 100 mg/kg and in all cases of the administration of 200 mg/kg of the compound No. 2, in five sixths case of the administration of 100 mg/kg and in two thirds case of the administration of 50 mg/kg of the compound No. 4, in two thirds case of the administration of 200 mg/kg of the compound No. 5, in a third case of each administration of 200 mg/kg of the compound No. 6 and the compound No. 7, in all cases of each administration of 200 mg/kg of the compound No. 50 and the compound No. 51, in two thirds case of the administration of 200 mg/kg of the compound No. 52 and a third case of the administration of 100 mg/kg, in five sixths case of the administration of 200 mg/kg of flunarizine. On the other hand, inhibitory activity against tonic extensive convulsion was observed in five sixths case of the administration of 25 mg/kg, all cases of the administrations of 100 mg/kg and 200 mg/kg of the positive control compound diphenylhydantoin. No inhibitory activity against tonic extensive convulsion was observed in case of the administration of 200 mg/kg of nimodipine.

TEST EXAMPLE 2

Activity against immobility time of forced swimming test in mice

In each group 6 Slc:ICR male mice weighing 25 to 32 g (5 weeks) were bred at the room temperature of 22° to 24° C. under an environment of 60% humidity for 1 week, and then the bred mice were subjected to the following test. The test was carried out by monitering action to voluntarily escape with TV camera when a mouse was put into a cylinder of which inner diameter was 11 cm wherein 17 cm of water being the temperature 25° C. as added. As indication immobility time for 6 minutes was measured. In the test mice were employed which were compulsorily swun for 6 minutes in once per day for continuous 3 day. The investigation for immobility time was carried out by measuring immobility time for 6 minutes 1 hour after oral administration of a test compound. Each of test compound was suspended in a 0.5% solution of methyl cellulose used as a control group. The results are shown in Table 4. Significant difference is shown with the significance level ( * : $p<0.05$) obtained by comparing data of control group by LSD method.

TABLE 4

| Test compound | Dose (mg/kg) | Immobility time (sec) |
|---|---|---|
| Control (0.5% methyl cellulose) | — | 240 ± 14 |
| Compound No. 2 (Example 2) | 12.5 | 248 ± 49 |
| | 25 | 258 ± 31 |
| | 50 | 204 ± 55 |
| | 100 | 190 ± 45* |
| Compound No. 4 (Example 24) | 50 | 134 ± 32* |
| | 100 | 127 ± 6* |
| | 200 | 148 ± 59* |
| Compound No. 5 (Example 25) | 200 | 136 ± 3* |
| Compound No. 6 (Example 4) | 200 | 153 ± 41* |
| Compound No. 7 (Example 26) | 200 | 127 ± 15* |
| Compound No. 50 (Example 28) | 200 | 149.4 ± 16.7* |
| Compound No. 51 (Example 29) | 200 | 139.5 ± 10.3* |
| Compound No. 52 (Example 30) | 200 | 190 ± 12.3* |
| Nimodipine | 25 | 265 ± 18 |
| | 50 | 266 ± 34 |
| | 100 | 245 ± 27 |
| | 200 | 220 ± 35 |
| Flunarizine | 100 | 227 ± 25 |

From Table 4, it is recognized that the compounds Nos. 2, 4, 5, 6, 7, 50, 51 and 52 of the present invention made the immobility time of forced swimming test reduced. As shown in Table 4, the administration of 100 mg/kg of the compound No. 2, the administrations of 200 mg/kg of the compounds Nos. 5, 6, 7, 50, 51 and 52 and the administrations of 50, 100 and 200 mg/kg of the compound No. 4 showed the effect on the immobility time. Nimodipine and flunarizine showed no effect.

TEST EXAMPLE 3

Activity against convulsion caused by pentylenetetrazole

In each group 4–8 Slc:ddy male mice weighing 24 to 32 g (5 weeks) were bred at room temperature of 22° to 24° C. under an environment of 60% humidity for 1 week, and then the bred mice were subjected to the following test. The test was carried out as the following procedure. One hour after the oral administration of a test compound, 40 mg/kg of pentylenetetrazole was administered in a caudal vein. Appearance of tonic extensive convulsion caused by pentylenetetrazole was measured as indication, and anticonvulsive activity was examined. Each of test compound was suspended in a 0.5% solution of methyl cellulose used as a control group. The results are shown in Table 5.

TABLE 5

| Test compound | Dose (mg/kg) | Number of appearance of tonic extensive convulsion |
|---|---|---|
| Control (0.5% methyl cellulose) | — | 8 cases/8 cases |
| Compound No. 2 | 6.25 | 3 cases/4 cases |
| | 12.5 | no case/4 cases |
| | 25 | 1 case/8 cases |
| Compound No. 2 | 50 | no case/8 cases |
| | 100 | no case/4 cases |
| Nimodipine | 25 | 3 cases/4 cases |
| | 50 | 1 case/4 cases |
| | 100 | 1 case/4 cases |
| Nicardipine | 25 | 4 cases/4 cases |
| | 50 | 1 case/4 cases |
| | 100 | no case/4 cases |
| Diphenylhydantoin | 6.25 | 2 cases/4 cases |
| | 12.5 | 1 case/4 cases |
| | 25 | 1 case/8 cases |
| | 50 | no case/8 cases |
| | 100 | no case/4 cases |

From Table 5, it is recognized that the compound No. 2 of the present invention inhibited the tonic extensive convulsion caused by pentylenetetrazole.

As shown in Table 5, the compound No. 2 of the present invention showed approximately the same extent of the effect of the positive control drug diphenylhydantoin, and showed stronger effect than the effect of nimodipine and the effect of nicardipine.

TEST EXAMPLE 4

Activity for blood pressure

In each group 4 Wister male rats weighing 200 to 300 g (10 to 15 weeks) were employed. The day before a test, rats were anesthetized with eter, and a polyethylene tube was inserted into aorta abdominalis of a rat. The other end of the polyethylene tube was led out of the rat's body. The led polyethylene tube was connected with a pressure transducer (RM-85, made by Yamamoto Kohden). Blood pressure was measured under a condition of no restriction.

The results are shown in Table 6.

TABLE 6

| | Blood pressure (mmHg) | | | |
|---|---|---|---|---|
| Test compound | After 15 min. | After 30 min. | After 60 min. | After 120 min. |
| Control (0.5% methyl cellulose) | 100.8 | 103.0 | 102.2 | 98.8 |
| Compound No. 2 (Example 2) (100 mg/kg)*1 | 100.6 | 98.4 | 94.8 | 92.9 |
| Compound No. 4 (Example 24) (100 mg/kg)*1 | 100.1 | 97.2 | 93.4 | 90.5 |
| Nicardipine (100 mg/kg)*1 | 100.0 | 67.2 | 69.2 | 67.2 |

[Note] *1: Dose of test compound by oral administration

As is clear from Table 6 the compounds Nos. 2 and 4 showed very weak activity for decreasing blood pressure. On the contrary, nicardipine showed remarkable activity for decreasing blood pressure.

TEST EXAMPLE 5

Activity against decapitation induced hypoxia in mice

In each group five Slc:ddy male mice weighing 20 to 22 g (4 weeks) were employed. Sixty minutes after oral administration of a test compound, mice were decapitated with a guillotine. After the decapitation, duration of gasping of head was measured with a timer (CT-916 Type, made by HATTORI SEIKO CO., LTD.) gearing into the guillotine.

Each of test compound was suspended in a 0.5% solution of methyl cellulose and administered. Inhibition rate was calculated by comparing with a 0.5% aqueous solution of methyl cellulose as control. That is, the inhibition rate was calculated by the following formula.

$$\text{Inhibition rate} = \frac{\text{Mean time of administration group} - \text{Mean time of control group}}{\text{Mean time of control group}} \times 100$$

The results are shown in Table 7.

TABLE 7

| Test compound | Dose (mg/kg, oral administration) | Inhibition rate (%) |
|---|---|---|
| Compound No. 2 (Example 2) | 10 | 10.8 |
|  | 30 | 20.5 |
| Compound No. 4 (Example 24) | 10 | 8.8 |
|  | 30 | 25.7 |
| Compound No. 50 (Example 28) | 100 | 31.1 |
| Compound No. 51 (Example 29) | 100 | 28.3 |
|  | 30 | 25.7 |
| Compound No. 52 (Example 30) | 100 | 26.4 |
| Nicardipine | 10 | 4.2 |
|  | 30 | 6.8 |
| Nimodipine | 10 | 2.1 |
|  | 30 | 9.3 |
| Flunarizine | 10 | 12.1 |
|  | 30 | 24.3 |

As is clear from Table 7, it was observed that the compounds Nos. 2 and 4 showed the same extent effect as that of flunarizine and showed stronger effect than that of nimodipine and that of nicardipine.

TEST EXAMPLE 6

Acute toxicity

The compound No. 2 of the present invention was orally administered to 5-15 in each group Slc:ddy male mice weighing 24 to 32 g (5 weeks). With death rate after 7 days value of acute toxicity was measured.
Result
Mouse $LD_{50} = 534$ mg/kg (oral administration)
It was demonstrated that the compound of the present invention has very low toxicity.

TEST EXAMPLE 7

Activity against cerebral blood flow in rabbits

In each group of dose 4 male rabbits (Japanese white native species) weighing 2.7 to 3.2 kg were employed. The rabbits were anesthetized by intravenously administering 1 g/kg of urethan. For administration of a drug a cannula was inserted and rabbits were fixed in a stereotaxical apparatus. Five minutes after the administration of a test compound, cerebral blood flow was measured by making a hole having diameter about 2.5 mm in cranial bone and clamping a probe of a laser doppler flowmeter (ALF 2100, made by Advance) on dura of back and side 1.5 to 2.5 mm of lobus parietalis cerebri cortex of apex at the time constant 1 sec by means of the present inventors own making constant-pressure clamp. The measured blood flow was recorded via a preamplifer (AD-600G, made by Nihon Kohden) in the recorder (AD-600G, made by Nihon Kohden).

The compound No. 2 of the present invention and flunarizine were dissolved in a 30% solution by macrogol 400 and intravenously administered in a dose of 0.5 mg/kg by body weight. As a control the solvent was administered in the same manner.

$$\text{Increase rate of cerebrocortical blood flow} = \frac{\text{Blood flow after administration} - \text{Blood flow before administration}}{\text{Blood flow before administration}} \times 100$$

The result are shown in FIG. 1.

In the following Examples, the identification of the compounds of the present invention was performed by means of melting point (mp), mass spectrum (MS), infrared absorption spectrum (IR) and $^1$H-NMR spectrum ($^1$H-NMR) and the like.

EXAMPLE 1

5-Ethoxycarbonyl-3-methoxycarbonyl-1,4-dihydro-2,6-dimethyl-4-(3-ethynylphenyl)pyridine In 20 ml of ethyl alcohol was dissolved 1.95 g (15 mmol) of 3-ethynylbenzaldehyde. Thereto were added 1.73 g (15 mmol) of methyl 3-aminocrotonate and 1.95 g (15 mmol) of ethyl acetoacetate. The mixture was stirred with heating for 16 hours at 80° C. After completing the reaction, the reaction solution was concentrated. The obtained precipitate was washed with ether and then recrystallized from the mixture solution of n-pentane and diethylether (n-pentane: diethylether =3 : 1 (by volume, hereinafter the same)) to give 3.5 g of the desired compound as yellow needle crystals (yield: 70%).

Hereinafter data of mp, MS and IR of the obtained compound are shown.

mp : 144°-145° C.
MS(m/z) : 339(M+), 324(M+—CH$_3$), 310(M+—C$_2$H$_5$),

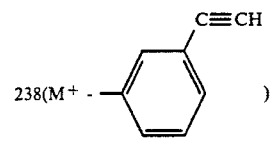

238(M+ — )

IR(KBr) (cm$^{-1}$) : 3320(>NH), 3000-2900(CH), 2100(—C≡CH), 1700(COO)

EXAMPLE 2

3,5-Diethoxycarbonyl-1,4-dihydro-2,6-dimethyl-4-(3-ethynylphenyl)pyridine

To the mixture of 3.9 g (0.03 mol) of 3-ethynylbenzaldehyde, 8.3 g (0.064 mol) of ethyl acetoacetate and 10 ml of ethyl alcohol was added 5 ml of 25-28% aqueous ammonia with stirring, and the reaction mixture was heated under reflux for 4 hours. After completing the reaction, the reaction solution was distilled away under reduced pressure. The residue was extracted with diethylether and washed with water, and was dehydrated. Then the residue was concentrated to give 5.2 g of yellow brown solid. To the solid was added the mixture solution of diethylether and n-pentane (diethylether: n-pentane=1 : 3 by volume). The mixture was crystallized to give 4.5 g of the desired compound (yield: 43%).

Hereinafter data of mp, MS, $^1$H-NMR and IR of the obtained compound are shown.

mp : 119°–120.5° C.

MS(m/z) : 353(M+), 324(M+—$C_2H_5$), 308(M+—$OC_2H_5$), 280(M+—$COOC_2H_5$) $^1$H-NMR($\delta$, ppm) (CDCl$_3$) 1.22(6H, t, J=16Hz, OCH$_2$C$\underline{H}_3$), 2.35(6H, s, C$\underline{H}_3$), 2.98(1H, s, C≡C$\underline{H}$), 4.10(4H, q, J=16Hz, OC$\underline{H}_2$CH$_3$), 4.98(1H, br, s, $\underline{H}$ of the 4-position), 5.75(1H, br, s, N$\underline{H}$), 7.18–7.52(4H, m, aromatic H)

IR(KBr) (cm$^{-1}$) : 3300(>NH), 2950–2900(CH), 2100(—C≡CH), 1700(COO)

EXAMPLE 3

3,5-Dimethoxycarbonyl-1,4-dihydro-2,6-dimethyl-4-(3-ethynylphenyl)pyridine

The procedure of reaction, treatment and purification of Example 2 were repeated except that 7.4 g (0.064 mol) of methyl acetoacetate was employed instead of ethyl acetoacetate employed in Example 2 to give 4.4 g of the desired compound (yield: 45%).

Hereinafter data of mp, MS and IR of the obtained compound are shown.

mp : 150°–151.5° C. MS(m/z) : 325(M+), 310(M+—CH$_3$), 294(M+—OCH$_3$), 266(M+—COOCH$_3$)

IR(KBr) (cm$^{-1}$) : 3300(>NH), 3000–2900(CH), 2100(—C≡CH), 1700(COO)

EXAMPLE 4

3,5-Diisopropoxycarbonyl-1,4-dihydro-2,6-dimethyl-4-(3-ethynylphenyl)pyridine

The procedure of reaction, treatment and purification of Example 2 were repeated except that 9.2 g (0.064 mol) of isopropyl acetoacetate was employed instead of ethyl acetoacetate employed in Example 2 to give 4.6 g of the desired compound (yield: 40%).

Hereinafter data of mp, MS and IR of the obtained compound are shown.

mp : 125°–127° C.

MS(m/z) : 381(M+), 338(M+—$C_3H_7$), 322(M+—$OC_3H_7$), 294(M+—$COOC_3H_7$)

IR(KBr) (cm$^{-1}$) : 3310(>NH), 3000–2900(CH), 2100(—C≡CH), 1700(COO)

EXAMPLE 5

3-Carboxy-5-ethoxycarbonyl-1,4-dihydro-2,6-dimethyl-4-(3-ethynylphenyl)pyridine

In 80 ml of ethyl alcohol was dissolved 7.5 g (0.02 mol) of 3,5-diethoxycarbonyl-1,4-dihydro-2,6-dimethyl-4-(3-ethynylphenyl)pyridine obtained in Example 2. Thereto was added 20 ml of 5N sodium hydroxide. After stirring for 24 hours at room temperature, the mixture was reacted further for 30 hours at 40°–45° C. After completing the reaction, the reaction solution was distilled away under reduced pressure. Water and chloroform were added to the residue, and a water layer was collected. The water layer was acidified with concentrated hydrochloric acid to give precipitate. The precipitate was purified by subjecting to silica gel column chromatography [eluent: chloroform-methyl alcohol (100 : 5)] to give 1.5 g of the desired compound (yield: 23.1%).

Also, the remainding chloroform layer was washed with water, dehydrated and concentrated to give 5.5 g of the starting compound (withdrawal: 73.3%).

Hereinafter data of mp, MS and IR of the obtained compound are shown. mp : 182°–183° C.

MS(m/z) : 325(M+)

IR(KBr) (cm$^{-1}$) : 3320(>NH), 3000–2900(CH), 2100(—C≡CH), 1680(COO), 1650–1640(COOH)

EXAMPLE 6

3-Carboxy-5-isopropoxycarbonyl-1,4-dihydro-2,6-dimethyl-4-(3-ethynylphenyl)pyridine The procedure of reaction, treatment and purification of Example 5 were repeated except that 7.6 g (0.02 mol) of 3,5-diisopropoxycarbonyl-1,4-dihydro-2,6-dimethyl-4-(3-ethynylphenyl)pyridine obtained in Example was employed instead of 3,5-diethoxycarbonyl-1,4-dihydro-2,6-dimethyl-4-(3-ethynylphenyl)pyridine employed in Example 5 to give 1.4 g of the desired compound (yield: 20%).

Hereinafter data of mp, MS and IR of the obtained compound are shown.

mp : 191°–193° C.

MS(m/z) : 339(M+)

IR(KBr) (cm$^{-1}$) : 3310( NH), 3100–2900(CH), 2100(—C≡CH), 1690(COO), 1660–1650(COOH)

EXAMPLE 7

Magnesium salt of 3-carboxy-5-ethoxycarbonyl-1,4-dihydro-2,6-dimethyl-4-(3-ethynylphenyl)pyridine In 20 ml of anhydrous methyl alcohol was dissolved 33.2 mg (1.38 mmol) of metal magnesium with stirring and heating. Thereto was added 0.9 g (2.77 mmol) of 3-carboxy-5-ethoxycarbonyl-1,4-dihydro-2,6-dimethyl-4-(3-ethynylphenyl)pyridine obtained in Example 5 which was dissolved in 50 ml of methyl alcohol. The admixture was reacted for 30 minutes at room temperature. After completing the reaction, the solvent was distilled away under reduced pressure to give precipitate. The precipitate was washed with ethylether and then dried to give 0.9 g of the desired compound (yield: 96.8%).

Hereinafter data of mp and IR of the obtained compound are shown.

mp : >300° C.

IR(KBr) (cm$^{-1}$) : 3310(>NH), 2950–290(CH), 2100(—C≡CH), 1680–1640(COO, COO$^-$)

EXAMPLE 8

Magnesium salt of 3-carboxy-5-isopropoxycarbonyl-1,4-dihydro-2,6-dimethyl-4-(3-ethynylphenyl)pyridine The procedure of reaction and treatment of Example 7 were repeated except that 0.94 g (2.77 mmol) of 3-carboxy-5-isopropoxycarbonyl-1,4-dihydro-2,6-dimethyl-4-(3-ethynylphenyl)pyridine obtained in Example 6 was employed instead of 3-carboxy-5-ethoxycarbonyl-1,4-dihydro-2,6-dimethyl-4-(3-ethynylphenyl)pyridine employed in Example 7 to give 0.9 g of the desired compound (yield: 92.8%).

Hereinafter data of mp and IR of the obtained compound are shown.

mp : >300° C.

IR(KBr) (cm$^{-1}$) : 3300(>NH), 3000–2900(CH), 2100(—C≡CH), 1690–1640(COO, COO$^-$)

EXAMPLE 9

5-Isopropoxycarbonyl-1,4-dihydro-2,6-dimethyl-3-methoxyethoxycarbonyl-4-(3-ethynylphenyl)pyridine In 30 ml of dry ethyl alcohol was dissolved 1.3 g (10 mmol) of 3-ethynylbenzaldehyde, and 1.43 g (10 mmol) of isopropyl 3-aminocrotonate and 1.6 g (10 mmol) of methoxyethyl acetoacetate were successively added thereto at room temperature. The admixture was reacted under reflux with heating for 12 hours. After completing the reaction, the reaction solution was distilled away under reduced pressure and purified by subjecting to silica gel column chromatography [eluent: n-hexane-chloroform (1 : 1) to chloroform]to give 2.1 g of the chloroform (1 : 1) to chloroform] to give 2.1 g of the desired compound (yield: 53%).

Hereinafter data of mp, MS and IR of the obtained compound are shown.

64.5°–66.5° C.

MS(m/z) : 397($M^+$),

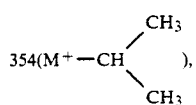

338($M^+-CH_2Ch_2OCH_3$),

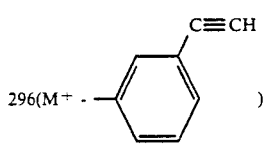

IR(KBr) ($cm^{-1}$) : 3300(>NH), 2960–2850(CH), 2100(—C≡CH), 1690(COO)

Example 10

[2-Amino-3,5-diethoxycarbonyl-1,4-dihydro-6-methyl-4-(3-ethynylphenyl)pyridine In 5 ml of dry ethyl alcohol was dissolved 4.5 g (18.6 mmol) of 2-(3-ethynylbenzylidene)-ethyl acetoacetate at room temperature, 4.8 g (37.2 mmol) of ethoxycarbonyl acetoamidine was added thereto. The admixture was reacted for 3 hours at room temperature. After completing the reaction, the solvent was distilled away. The residue was dissolved in dichloromethane and successively washed with water and saturated solution of salt. After drying the organic layer, the solvent was distilled away under reduced pressure, and the residue was purified by subjecting to silica gel column chromatography [eluent: hexane-ethyl acetate (85 : 15 to 60 : 40)] to give 4.9 g of the desired compound as white yellow crystals (yield: 74%).

Hereinafter data of mp, MS, $^1$H-NMR and IR of the obtained compound are shown.

mp : 112°–114° C.

MS(m/z) : 354($M^+$), 325($M^+-C_2H_5$), 309($M^+-OC_2H_5$), 281($M^+-COOC_2H_5$),

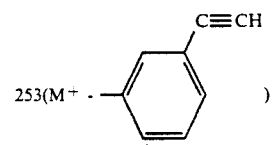

$^1$H-NMR (δ, ppm) (CDCl$_3$) : 1.20(6H, t, —CH$_2$CH$_3$), 2.27(3H, s, —CH$_3$), 3.02(1H, s, —C≡CH), 4.13(4H̄, q, —CH$_2$CH$_3$), 4.93(1H, s, H of the 4-position), 6.23(2H, br, s, —NH$_2$), 7.20(1H, br, s, —NH̄), 7.23–8.02(4H, m, aromatic H̄)

IR(KBr) ($cm^{-1}$) : 3400(NH$_2$, >NH), 3320–3250(NH$_2$,>NH), 3000–2900(CH), 2100(—C≡CH), 1710–1690(COO)

EXAMPLE 11

2-Amino-3,5-dimethoxycarbonyl-1,4-dihydro-6-methyl-4-(3-ethynylphenyl)pyridine The procedure of reaction, treatment and purification of Example 10 were repeated except that 4.2 g (18.6 mmol) of 2-(3-ethynylbenzylidene)-methyl acetoacetate was employed instead of 2-(3-ethynylbenzylidene)-ethyl acetoacetate employed in Example 10, and 4.3 g (37.2 mmol) of methoxycarbonyl acetoamidine was employed instead of ethoxycarbonyl acetoamidine employed in Example 10 to give 4.6 g of the desired compound (yield: 77%).

Hereinafter data of mp, MS and IR of the obtained compound are shown.

mp : 121°–122° C.

MS(m/z) : 326($M^+$), 311($M^+-CH_3$), 295($M^+-OCH_3$), 267($M^+-COOCH_3$), 253($M^+-COOCH_3-CH_2$)

IR(KBr) ($cm^{-1}$) : 3410(CONH$_2$, >NH), 3300–3250(NH$_2$>NH), 3000–2900(CH), 2100(—C≡CH), 1700–1685(COO)

EXAMPLE 12

2-Amino-3-ethoxycarbonyl-5-cyclohexylcarboxy-1,4-dihydro-6-methyl-4-(3-ethynylphenyl)pyridine In 50 ml of dry ethyl alcohol was dissolved 1.95 g (15 mmol) of 3-ethynylbenzaldehyde, 1.95 g (15 mmol) of ethoxycarbonyl acetoamidine and 2.76 g (15 mmol) of cyclohexyl acetoacetate were added thereto. The admixture was reacted for 10 hours at 90° C. After completing the reaction, the solvent was distilled away under reduced pressure. The residue was purified by subjecting to silica gel column chromatography [eluent: n-hexane-ethyl acetate (9 : 1 to 7 : 3)] to give 1.7 g of the desired compound (yield: 27.7%).

Hereinafter data of mp, MS and IR of the obtained compound are shown.

mp : 53°–55° C.

MS(m/z) : 408($M^+$), 335($M^+-COOC_2H_5$),

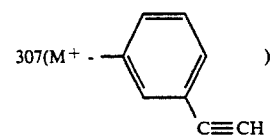

IR(KBr) ($cm^{-1}$) : 3420(CONH$_2$,>NH), 3300–3250(NH$_2$, NH), 2950–2850(CH), 2100(—C≡CH), 1680–1670(COO)

EXAMPLE 13

2-Amino-3-ethoxycarbonyl-5-methoxycarbonyl-1,4-dihydro-6-methyl-4-(3-ethynylphenyl)pyridine The procedure of reaction, treatment and purification of Example 12 were repeated except that 2.2 g (18.6 mmol) of methyl acetoacetate was employed instead of cyclohexyl acetoacetate employed in Example 12 to give 1.8 g of the desired compound (yield: 35%).

Hereinafter data of mp, MS and IR of the obtained compound are shown.

mp : 102+≧104° C.

MS(m/z) : 340(M+), 267(M+—COOC$_2$H$_5$),

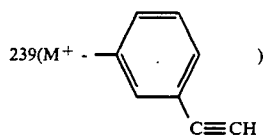
239(M+ - ⟨phenyl-C≡CH⟩)

IR(KBr) (cm$^{-1}$) : 3410(CONH$_2$,>NH), 3310-3250(NH$_2$, NH), 3000-2900(CH), 2100(—C≡CH), 1690-1670(COO)

EXAMPLE 14

3,5-Dimethoxycarbonyl-1,4-dihydro-6-methyl-2-dimethoxymethyl-4-(3-ethynylphenyl)pyridine The mixture of 3.74 g (0.014 mol) of 2-(3-ethynylbenzylidene)-4,4-dimethoxy-methyl acetoacetate and 1.6 g (0.014 mol) of methyl-3-aminocrotonate was stirred with heating for 1 hour at 70° C., then for 1 hour at 100° C., further for 3 hours at 120° C. After completing the reaction, the reaction mixture was dissolved in ethylacetate. After the solution was washed with water and dehydrated, the solvent was distilled away under reduced pressure to give 4.3 g of the desired compound as yellow oil (yield: 79.6%).

Hereinafter data of MS, $^1$H-NMR and IR of the obtained compound are shown.

MS(m/z) : 385(M+), 354(M+—OCH$_3$), 295(M+—COOCH$_3$—OCH$_3$) $^1$H—NMR(δ, ppm) (CDCl$_3$) 2.3(3H, s, —CH$_3$), 3.0(1H, s, —C≡CH), 3.4(3H, s, —OCH$_3$), 3.5(3H, s, —OCH$_3$), 3.62(3H, s, —COOCH$_3$), 3.68(3H, s, —COOCH$_3$), 5.1(1H, s, H of the 4-position), 6.0(1H, s, —CH(OCH$_3$)$_2$), 6.8(1H, br, s, NH), 7.5-7.0(4H, m, aromatic H)

IR(neat) (cm$^{-1}$) : 3310 (>NH), 2900-2850(CH), 2100(—C≡CH), 1700(COO)

EXAMPLE 15

3,5-Dimethoxycarbonyl-2-formyl-1,4-dihydro-6-methyl-4-(3-ethynylphenyl)pyridine

The mixture of 4.3 g (0.011 mol) of 3,5-dimethoxycarbonyl-1,4-dihydro-6-methyl-2-dimethoxymethyl-4-(3-ethynylphenyl)pyridine obtained in Example 14, 5 ml of 6N hydrochloric acid and 50 ml of acetone was stirred for 4 hours at room temperature. After completing the reaction, acetone was distilled away, water was added to the residue. Then pH of the solution was adjusted to 7.5 with saturated solution of sodium hydrogencarbonate. The solution was extracted with ethyl acetate several times. All organic layers thereof were mixed, and were washed with water, dehydrated and concentrated. Then, the residue was purified by subjecting to silica gel column chromatography [eluent: benzene-ethyl acetate (5 : 4)] and recrystallized from ethyl acetate to give 2.4 g of the desired compound as yellow prism crystals (yield: 64.9%).

Hereinafter data of mp, MS, $^1$H-NMR and IR of the obtained compound are shown.

mp : 100°-101.5° C.

MS(m/z) : 339(M+), 308(M+—OCH$_3$), 280(M+—COOCH$_3$) $^1$H-NMR(δ, ppm) (CDC$_3$) 2.45(3H, s, —CH$_3$), 3.1(1H, s, —C≡CH), 3.7(3H, s, —COOCH$_3$), 3.8(3H, s, —COOCH$_3$), 5.2 (1H, s, H of the 4-position), 7.1(1H, br, s, NH), 7.32-7.46(4H, m, aromatic H) 10.6(1H, s, CHO)

IR(KBr) (cm$^{-1}$) : 3320(>NH), 2900-2850(CH), 2100(—C≡CH), 1700(COO), 1680(CHO)

EXAMPLE 16

2-Cyano-3,5-dimethoxycarbonyl-1,4-dihydro-6-methyl-4-(3-ethynylphenyl)pyridine

In 16 ml of acetic acid was dissolved 1.87 g (5.5 mmol) of 3,5-dimethoxycarbonyl-2-formyl-1,4-dihydro-6-methyl-4-(3-ethynylphenyl)pyridine obtained in Example 15. Thereto were added 0.45 g (6.5 mmol) of hydroxylamine hydrochloride and 0.67 g (8.2 mmol) of sodium acetate. The admixture was stirred for 2.5 hours at room temperature. Then 1.96 g (19.2 mmol) of acetic anhydride was added thereto, and the admixture was reacted for 1.5 hours at room temperature, further for 4 hours at 95°-100° C. After completing the reaction, the reaction solution was concentrated under reduced pressure, water was added to the residue. After neutralization of the reaction mixture with saturated solution of sodium hydrogencarbonate, the reaction mixture was extracted with ethyl acetate several times. The organic layer thereof was washed with water, dehydrated and concentrated. The residue was purified by subjecting to silica gel column chromatography [eluent: benzene-ethyl acetate (10 : 1)] and recrystallized from the mixture of ethyl acetate and n-hexane to give 1.2 g of the desired compound as yellow prism crystals (yield: 66.7%).

Hereinafter data of mp, MS, $^1$H-NMR and IR of the obtained compound are shown.

mp : 169°-170° C.

MS(m/z) : 336(M+), 321(M+—CH$_3$), 277(M+—COOCH$_3$)

$^1$H-NMR(δ, ppm) (CDCl$_3$) 2.4(3H, s, CH$_3$), 3.08(1H, s, C≡CH), 3.68(3H, s, —COOCH$_3$), 3.82(3H, s, —COOCH$_3$), 5.15(1H, s, H of the 4-position), 7.0(1H, br, s, NH), 7.35-7.45(4H, m, aromatic H)

IR(KBr) (cm$^{-1}$) : 3250(>NH), 3000-2900(CH), 2250(CN), 2100(—C≡CH), 1710(COO)

EXAMPLE 17

3,5-Diethoxycarbonyl-1,4-dihydro-6-methyl-2-dimethoxymethyl-4-(3-ethynylphenyl)pyridine The procedure of reaction, treatment and purification of Example 14 were repeated except that 4.0 g (0.014 mol) of 2-(3-ethynylbenzylidene)-4,4-dimethoxyethyl acetoacetate was employed instead of 2-(3-ethynylbenzylidene)-4,4-dimethoxy-methyl acetoacetate employed in Example 14, and 1.8 g (0.014 mol) of ethyl-3-aminocrotonate was employed instead of methyl-3-aminocrotonate employed in Example 14 to give 4.4 g of the desired compound (yield: 75%).

Hereinafter data of MS and IR of the obtained compound are shown.

MS(m/z) : 413(M+), 368(M+—OC$_2$H$_5$), 295(M+—COOC$_2$H$_5$—OC$_2$H$_5$)

IR(neat) (cm$^{-1}$) : 3300(>NH), 2950–2850(CH), 2100(—C≡CH), 1700(COO)

EXAMPLE 18

3,5-Diethoxycarbonyl-2-formyl-1,4-dihydro-6-methyl-4-(3-ethynylphenyl)pyridine

The procedure of reaction, treatment and purification of Example 15 were repeated except that 4.5 g (0.011 mol) of 3,5-diethoxycarbonyl-1,4-dihydro-6-methyl-2-dimethoxymethyl-4-(3-ethynylphenyl)pyridine obtained in Example 17 was employed instead of 3,5-dimethoxycarbonyl-1,4-dihydro-6-methyl-2-dimethoxymethyl-4-(3-ethynylphenyl)pyridine to give 2.4 g of the desired compound (yield: 60%).

Hereinafter data of mp, MS and IR of the obtained compound are shown.

mp : 109°–111° C.

MS(m/z) : 367(M$^+$), 322(M$^+$—OC$_2$H$_5$), 294(M$^+$—COOC$_2$H$_5$)

IR(KBr) (cm$^{-1}$) : 3320(>NH), 3000–2900(CH), 2100(—C≡CH), 1700(COO), 1690–1680(CHO)

EXAMPLE 19

2-Cyano-3,5-diethoxycarbonyl-1,4-dihydro-6-methyl-4-(3-ethynylphenyl)pyridine

The procedure of reaction, treatment and purification of Example 16 were repeated except that 2.0 g (5.5 mmol) of 3,5-diethoxycarbonyl-2-formyl-1,4-dihydro-6-methyl-4-(3-ethynylphenyl)pyridine obtained in Example 18 was employed instead of 3,5-dimethoxycarbonyl-2-formyl-1,4-dihydro-6-methyl-4-(3-ethynylphenyl)pyridine to give 1.4 g of the desired compound (yield: 68%).

Hereinafter data of mp, MS and IR of the obtained compound are shown.

mp : 176°–178° C.

MS(m/z) : 364(M$^+$), 335(M$^+$—C$_2$H$_5$), 291(M$^+$—COOC$_2$H$_5$)

IR(KBr) (cm$^{-1}$) : 3250(>NH), 3000–2900(CH), 2250(CN), 2100(—C≡CH), 1700(COO)

EXAMPLE 20

3-t-Butoxycarbonyl-5-ethoxycarbonyl-1,4-dihydro-2,6-dimethyl-4-(3-ethynylphenyl)pyridine In 5 ml of ethyl alcohol was dissolved 1.95 g (0.008 mol) of 2-(3-ethynylbenzylidene)-ethyl acetoacetate. Thereto were added 1.58 g (0.01 mol) of t-butyl acetoacetate, 0.77 g (0.01 mol) of ammonium acetate and 25 m: of ethyl alcohol. The admixture was reacted under reflux with heating for 1 hour. After completing the reaction, the reaction solution was distilled away under reduced pressure, the residue was purified by subjecting to silica gel column chromatography [eluent: n-hexane-ethyl acetate (7 : 1 to 5 : 1)] to give 0.7 g of the desired compound (yield: 23.3%).

Hereinafter data of mp, MS and IR of the obtained compound are shown.

mp : 80.5°–82.5° C.

MS(m/z) : 381(M$^+$), 324(M$^+$—t-Bu),

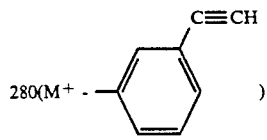

IR(KBr) (cm$^{-1}$) : 3300(>NH), 3000–2900(CH), 2100(—C≡CH), 1700–1670(COO)

EXAMPLE 21

3,5-Di-t-butoxycarbonyl-1,4-dihydro-2,6-dimethyl-4-(3-ethynylphenyl)pyridine

The procedure of reaction and treatment of Example 2 were repeated except that 10.1 g (0.064 mol) of t-butyl acetoacetate was employed instead of ethyl acetoacetate employed in Example 2 and the reaction was carried out for 6 hours instead of 4 hours. The reaction solution was purified by subjecting to silica gel column chromatography [eluent: n-hexane-ether-chloroform (3 : 1 9 to 2 : 1 : 9)] to give 6.6 g of the desired compound (yield: 53.8%).

Hereinafter data of mp, MS and IR of the obtained compound are shown.

mp : 151.5°–152.0° C.

MS(m/z) : 409(M$^+$),

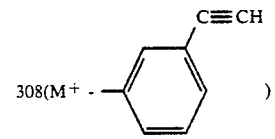

IR(KBr) (cm$^{-1}$) : 3300(>NH), 3000–2900(CH), 2100(—C≡CH), 1700(COO)

EXAMPLE 22

5-Carbamoyl-3-methoxycarbonyl-1,4-dihydro-2,6-dimethyl-4-(3-ethynylphenyl)pyridine The procedure of reaction, treatment and purification of Example 1 were repeated except that 1.5 g (15 mmol) of acetoacetoamido was employed instead of ethyl acetoacetate employed in Example 1 to give 2.3 g of the desired compound (yield: 50%).

Hereinafter data of mp, MS and IR of the obtained compound are shown.

mp : 215°–217° C.

MS(m/z) : 310(M$^+$), 295(M$^+$—CH$_3$),

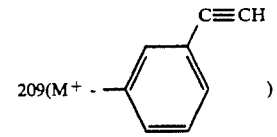

IR(KBr) (cm$^{-1}$) : 3500(CONH$_2$, >NH), 3400–3300-(CONH$_2$, >NH), 3000–2900(CH), 2100(—C≡CH), 1700–1690(COO, $\underline{C}$ONH$_2$)

EXAMPLE 23

5-N-Methylcarbamoyl-3-methoxycarbonyl-1,4-dihydro-2,6-dimethyl-4-(3-ethynylphenyl)pyridine The procedure of reaction, treatment and purification of Example 1 were repeated except that 1.7 g (15 mmol) of N-methyl acetoacetoamido was employed instead of ethyl acetoacetate employed in Example 1 to give 2.5 g of the desired compound (yield: 51%).

Hereinafter data of mp, MS and IR of the obtained compound are shown.

mp : 271°–273° C.

MS(m/z) : 324(M$^+$), 309(M$^+$—CH$_3$),

223(M+ — 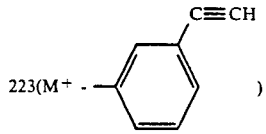)

IR(KBr) (cm⁻¹) : 3440(CONH₂,>NH), 3400-3300-(CONH₂,>NH), 3000-2900(CH), 2100(—C≡CH), 1700-1680(COO, CONH₂)

EXAMPLE 24

5-Ethoxycarbonyl-3-isopropoxycarbonyl-1,4-dihydro-2,6-dimethyl-4-(3-ethynylphenyl)pyridine To a mixture of 0.65 g (0.005 mol) of 3ethynylbenzaldehyde, 1.08 g (0.0075 mol) of isopropyl acetoacetate and 25 ml of isopropyl alcohol were added 2 to 3 drops of piperidine. After heating the mixture under reflux for 24 hours, 0.65 g (0.005 mol) of ethyl 3-aminocrotonate was added thereto, further the admixture was heated under reflux for 24 hours. After completing the reaction, the reaction mixture was concentrated. The obtained precipitate was purified by subjecting to silica gel column chromatography [eluent: n-hexane to n-hexane: ethyl acetate (7 : 3)] to give 1.1 g of the desired compound (yield: 58.6%).

Hereinafter data of mp, MS and IR of the obtained compound are shown.
mp : 96°-97° C.
MS(m/z) : 367(M+), 352(M+—CH₃), 324(M+—C₃H₇), 322(M+—OC₂H₅), 308(M+—OC₃H₇)
IR(KBr) (cm⁻¹) : 3350-3250(>NH), 2950-2850(CH), 2100(—C≡CH), 1670(COO)

EXAMPLE 25

5-Ethoxycarbonyl-3-n-propoxycarbonyl-1,4-dihydro-2,6-dimethyl-4-(3-ethynylphenyl)pyridine The procedure of reaction and treatment of Example 1 were repeated except that 1.94 g (15 mmol) of ethyl 3-aminocrotonate was employed instead of methyl 3-aminocrotonate employed in Example 1 and 2.2 g (15 mmol) of n-propyl acetoacetate was employed instead of ethyl acetoacetate employed in Example 1 to give 3.7 g of the desired compound (yield: 67.0%).

Hereinafter data of mp, MS and IR of the obtained compound are shown.
mp : 120°-121° C.
MS(m/z) : 367(M+), 338(M+—C₂H₅), 322(M+—OC₂H₅), 308(M+—OC₃H₇)
IR(KBr) (cm⁻¹) : 3330-3230(>NH), 3000-2900(CH), 2100(—C≡CH), 1700(COO)

EXAMPLE 26

5-Isopropoxycarbonyl-3-methoxycarbonyl-1,4-dihydro-2,6-dimethyl-4-(3-ethynylphenyl)pyridine The procedure of reaction, treatment and purification of Example 24 were repeated except that 0.64 g (0.005 mol) of methyl 3-aminocrotonate was employed instead of ethyl 3-aminocrotonate employed in Example 24 to give 0.95 g of the desired compound (yield: 56%).

Hereinafter data of mp, MS and IR of the obtained compound are shown.
mp : 95°-98° C.
MS(m/z) : 353(M+), 338(M+—CH₃)

IR(KBr) (cm⁻¹) : 3350-3250(>NH), 2950-2850(CH), 2100(—C≡CH), 1670(COO)

EXAMPLE 27

5-Ethoxycarbonyl-3-sec-butoxycarbonyl-1,4-dihydro-2,6-dimethyl-4-(3-ethynylphenyl)pyridine The procedure of reaction and treatment of Example 25 were repeated except that 2.4 g (15 mmol) of sec-butyl acetoacetate was employed instead of n-propyl acetoacetate employed in Example 25 to give 3.6 g of the desired compound (yield: 63.2%).

Hereinafter data of mp, MS and IR of the obtained compound are shown.
mp : 105°-106° C.
MS(m/z) : 381(M+), 366(M+—CH₃), 352(M+—C₂H₅), 336(M+—OC₂H₅), 308(M+—OC₄H₉)
IR(KBr)(cm⁻¹) : 3320-3250 (>NH), 3000-2880(CH), 2100(—C≡CH), 1700(COO)

EXAMPLE 28

5-Ethoxycarbonyl-3-allyloxycarbonyl-1,4-dihydro-2,6-dimethyl-4-(3-ethynylphenyl)pyridine In 20 ml of ethyl alcohol was dissolved 1.95 g (15 mmol) of 3-ethynylbenzaldehyde. Thereto were added 1.95 g (15 mmol) of ethyl 3-aminocrotonate and 2.1 g (15 mmol) of allyl acetoacetate, and the admixture was stirred with heating for 16 hours at 80° C. After completing the reaction, the reaction mixture was concentrated to give precipitate. After washing the obtained precipitate with ether, the precipitate was recrystallized from the mixture solution of n-pentane and diethyl ether (n-pentane : diethyl ether=3 : 1 by volume) to give 3.4 g of the desired compound of light yellow needle crystal (yield: 61.5%).

Hereinafter data of mp, MS and IR of the obtained compound are shown.
mp : 121°-122° C.
MS(m/z) : 365(M+), 336(M+—C₂H₅), 320(M+—OC₂H₅), 308(M+—OCH₂CH=CH₂)
IR(KBr)(cm⁻¹) : 3300-3220(>NH), 2970-2850(CH), 2100(—C≡CH), 1700(COO)

EXAMPLE 29

5-Ethoxycarbonyl-3-crotyloxycarbonyl-1,4-dihydro-2,6-dimethyl-4-(3-ethynylphenyl)pyridine The procedure of reaction and treatment of Example 28 were repeated except that 2.34 g (15 mmol) of crotyl acetoacetate was employed instead of allyl acetoacetate employed in Example 28 to give 3.1 g of the desired compound (yield: 54%).

Hereinafter data of mp, MS and IR of the obtained compound are shown.
mp : 125°-128° C.
MS(m/z) : 379(M+), 350(M+—C₂H₅), 334(M+—OC₂H₅), 308(M+—OCH₂CH=CH₂CH₃)
IR(KBr)(cm⁻¹) : 3300-3220(>NH), 2970-2850(CH), 2100(—C≡CH), 1700(COO)

EXAMPLE 30

5-Methoxycarbonyl-3-(3-methyl-2-butenyl oxycarbonyl)-1,4-dihydro-2,6-dimethyl-4-(3-ethynylphenyl)pyridine The procedure of reaction and treatment of Example 28 were repeated except that 1.73 g (15 mmol) of methyl 3-aminocrotonate was employed instead of ethyl 3- aminocrotonate in Example 28, and 2.55 g (15 mmol) of 3-methyl-2-butenyl acetoacetate was employed instead of allyl acetoacetate employed in Example 28 to give 2.9 g of the desired compound (yield: 50%).

Hereinafter data of mp, MS and IR of the obtained compound are shown.

mp : 127°-130° C.

MS(m/z) : 379(M$^+$), 364(M$^+$—CH$_3$), 348(M$^+$—OCH$_3$), 308(M$^+$—OCH$_2$CH=C(CH$_3$)$_2$)

IR(KBr)(cm$^{-1}$) : 3300-3220(>NH), 2970-2850(CH), 2100(—C≡CH), 1700(COO)

Formulation Examples of cerebral function improver of the present invention are shown as follows.

FORMULATION EXAMPLE 1

In a centrifugal flow system for agglomerating, glanulating and coating, 960 g of lactose (100 mesh) was sprayed and coated with 1000 ml of the solution of ethanol and methylene chloride (ethanol : methylene chloride =1 : 1, v/v) in which 10 g of the compound No. of the present invention and 30 g of hydroxypropyl methyl cellulose were completely dissolved to give granules according to a conventional method. After drying them for 4 hours at 40° C., the compound No. 2 was granulated to give a granule according to a conventional method.

FORMULATION EXAMPLE 2

In a centrifugal flow system for agglomerating, glanulating and coating, 1590 g of lactose (100 mesh) was sprayed and coated with 5000ml of the solution of ethanol and methylene chloride (ethanol : methylene chloride=1 : 1, v/v) in which 100 g of the compound No. 2 of the present invention and 300 g of hydroxypropyl methyl cellulose were completely dissolved to give granules according to a conventional method. After drying them for 4 hours at 40° C., the compound No. 2 was granulated according to a conventional method. After 10 g of magnesium stearate was added thereto and mixed, the mixture was filled up into capsules to give a capsule.

FORMULATION EXAMPLE 3

In 200 ml of ethanol were dissolved 10 g of the compound No. 2 of the present invention and 30 g of polyvinyl pyrrolidone, and then ethanol was distilled away with drying under reduced pressure. The residue was pulverized to powder. Thereto were added 20 g of lactose, 19 g of calcium carboxymethanol and 1 g of magnesium stearate. According to a conventional method, the mixture was compressed to give tablets containing 10 mg of the compound No. 2 per tablet.

FORMULATION EXAMPLE 4

The powder obtained in Formulation Example 3, 50 g of corn starch, 60 g of lactose and gelatinized starch were mixed to give granules. Thereto was added 2 g of magnesium stearate, and the mixture was compressed according to a conventional method to give sublingual tablets containing 10 mg of the compound No. 2 per tablet.

FORMULATION EXAMPLE 5

To the mixture solution of 50 g of microcrystalline wax fused with heating and 100 g of paraffin was added 40 g of white soft paraffin, and the mixture was kneaded together and transferred into a chaser mill. Separately, isopropyl myristate solution containing 10 g of the compound No. 2 of the present invention was prepared. The prepared solution was gradually added to the mixture with stirring. The mixture was kneaded to give an ointment.

FORMULATION EXAMPLE 6

In 150 ml of 90% ethanol was dissolved the compound No. 2 of the present invention. Then the solution was added to the distilled water for injection containing 150 ml of propylene glycol, 2 g of sodium citrate and 0.3 g of citric acid to give total amount of 600 ml of an injection.

FORMULATION EXAMPLE 7

Various components such as 5 g of the compound No. 2 of the present invention, 25 g of polyvinyl pyrrolidone, 5 g of polyethylene glycol 400, 25 g of magnesium alumino meta silicate, 137 g of starch and anhydrous calcium phosphate (starch : anhydrous calcium phosphate=8 : 2) and 1 g of magnesium stearate were mixed in such proportion and compressed with shaping to give tablets containing 5 mg of the compound No. 2 per tablet according to a conventional method.

In addition to the ingredients used in the Examples and the Formulation Examples, other ingredients can be used in the Examples and the Formulation Examples as set forth in the specification to obtain substantially the same results.

What we claim is:

1. A 1,4-dihydropyridine derivative having the formula (I):

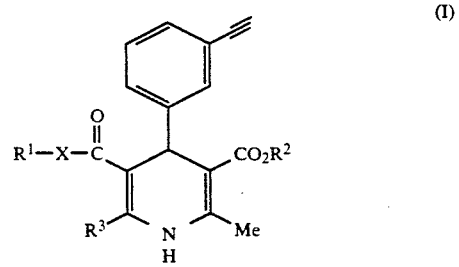

wherein X is oxygen atom; R$^1$ is a lower alkyl group, a lower cycloalkyl group, or a lower alkenyl group; R$^2$ is a lower alkyl group, a lower cycloalkyl group or a lower alkoxyalkyl group; and R$^3$ is a formyl group, dimethoxymethyl group, cyano group or amino group; or a pharmaceutically acceptable salt thereof.

2. The 1,4-dihydropyridine derivative or a pharmaceutically acceptable salt thereof of claim 1, wherein R$^3$ is amino group.

3. The 1,4-dihydropyridine derivative or a pharmaceutically acceptable salt thereof of claim 1, wherein R$^3$ is cyano group.

4. The 1,4-dihydropyridine derivative or a pharmaceutically acceptable salt thereof of claim 1, wherein R$^3$ is formyl group.

5. The 1,4-dihydropyridine derivative or a pharmaceutically acceptable salt thereof of claim 1, wherein R$^3$ is dimethoxymethyl group.

6. A 1,4-dihydropyridine derivative having the formula (I):

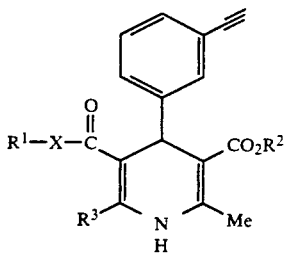

(I)

wherein X is oxygen atom; $R^1$ is an alkyl group having 2-3 carbon atoms, a lower cycloalkyl group or a lower alkenyl group; $R^2$ is an alkyl group having 2-3 carbon atoms, a lower cycloalkyl group or a lower alkoxyalkyl group; and $R^3$ is a lower alkyl group; or a pharmaceutically acceptable salt thereof.

7. The 1,4-dihydropyridine derivative or a pharmaceutically acceptable salt thereof of claim 6, wherein $R^1$ and $R^2$ are the same or different and each of $R^1$ and $R^2$ is an alkyl group having 2-3 carbon atoms, and $R^3$ is a lower alkyl group.

8. The 1,4-dihydropyridine derivative or a pharmaceutically acceptable salt thereof of claim 6, wherein $R^1$ and $R^2$ are the same or different and each is an alkyl group having 2-3 carbon atoms.

9. The 1,4-dihydropyridine derivative or a pharmaceutically acceptable salt thereof of claim 6, wherein $R^1$ is a lower cycloalkyl group.

10. The 1,4-dihydropyridine derivative or a pharmaceutically acceptable salt thereof of claim 6, wherein $R^2$ is a lower alkoxyalkyl group.

11. The 1,4-dihydropyridine derivative or a pharmaceutically acceptable salt thereof of claim 6, wherein $R^2$ is an alkyl group having 2-3 carbon atoms.

12. The 1,4-dihydropyridine derivative or a pharmaceutically acceptable salt thereof of claim 6, wherein $R^2$ is a lower cycloalkyl group.

13. The 1,4-dihydropyridine derivative or a pharmaceutically acceptable salt thereof of claim 6, wherein $R^1$ is a lower alkenyl group.

14. A 1,4-dihydropyridine derivative having the formula (I):

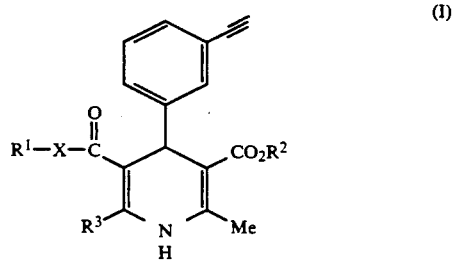

(I)

wherein X is oxygen atom, $R^1$ and $R^2$ are ethyl groups and $R^3$ is methyl group; or a pharmaceutically acceptable salt thereof.

15. A pharmaceutical composition for improving cerebral function which comprises as an effective ingredient the 1,4-dihydropyridine derivative or a pharmaceutically acceptable salt thereof of claim 6.

16. A pharmaceutical composition for improving cerebral function which comprises an effective amount of the 1,4-dihydropyridine derivative or a pharmaceutically acceptable salt thereof of claim 6 and a pharmaceutically acceptable carrier.

* * * * *